(12) United States Patent
Horii

(10) Patent No.: US 7,462,358 B2
(45) Date of Patent: Dec. 9, 2008

(54) ANTIGENIC POLYPEPTIDE SE36 OF MALARIA PLASMODIUM, PROCESS FOR PURIFICATION THEREOF, AND VACCINE AND DIAGNOSTIC AGENT USING THE ANTIGEN

(75) Inventor: Toshihiro Horii, Osaka (JP)

(73) Assignee: The Research Foundation for Microbial Diseases of Osaka, Osaka (JP)

( * ) Notice: Subject to any disclaimer, the term of this patent is extended or adjusted under 35 U.S.C. 154(b) by 0 days.

(21) Appl. No.: 11/517,455

(22) Filed: Sep. 8, 2006

(65) Prior Publication Data

US 2007/0009994 A1    Jan. 11, 2007

Related U.S. Application Data

(63) Continuation of application No. 10/239,517, filed as application No. PCT/JP02/00506 on Jan. 24, 2002, now abandoned.

(30) Foreign Application Priority Data

Jan. 24, 2001    (JP)    ............... 2001-057458

(51) Int. Cl.
 A61K 39/015    (2006.01)
 A61K 45/00    (2006.01)
 C07K 1/00    (2006.01)
 C07H 21/02    (2006.01)
(52) U.S. Cl. .............. 424/268.1; 424/278.1; 424/272.1; 530/350; 530/355; 536/23.1
(58) Field of Classification Search ................. 530/350, 530/355; 536/23.1; 424/278.1, 268.1, 272.1
 See application file for complete search history.

(56) References Cited

U.S. PATENT DOCUMENTS

| | | | |
|---|---|---|---|
| 5,395,614 | A | 3/1995 | Knapp et al. |
| 6,024,966 | A | 2/2000 | Inselburg et al. |
| 6,333,406 | B1 | 12/2001 | Inselburg et al. |

FOREIGN PATENT DOCUMENTS

| | | | |
|---|---|---|---|
| EP | 0 283 882 | | 9/1988 |
| NZ | 223907 | | 5/1991 |
| WO | WO 90/01549 | * | 2/1990 |

OTHER PUBLICATIONS

Sugiyama et al., Vaccine, 1996; 14(11): 1069-1076.*
T. Horii et al., "Protective Immunity Induced in Squirrel Monkeys with Recombinant Serine Repeat Antigen (SERA) of *Plasmodium falciparum*", *Parasitology International*, vol. 46, pp. 17-25, 1997.
B. Knapp et al., "A New Blood Stage Antigen *Plasmodium falciparum* highly Homologous to the Serine-Stretch Protein SERP", *Mol. Biochem Parasitol*, vol. 44, No. 1, pp. 1-13, Jan. 1991.

Biosis on STN, Accession No. 1999:484731, T. Horii et al., "Immune Responses Induced by Gene Gun or Intramuscular Injection of DNA Vaccines that Express Immunogenic Regions of the Serine Repeat Antigen from *Plasmodium falciparum*", *Infect Immun.*, vol. 67, No. 10, pp. 5163-5169, Oct. 1999.
Biosis on STN, Accession No. 1999:232590, T. Horii et al., "Antibodies Reactive with the N-terminal Domain of *Plasmodium falciparum* Serine Repeat Antigen Inhibit Cell Proliferation by Agglutinating Merozoites and Schizonts", *Infect Immun.*, vol. 67, No. 4, pp. 1821-1827, Apr. 1999.
T. Horii, "Malaria Gencyu Kisei no Bunshi Senryaku to Vaccine no kaihatsu", *Protein, Nucleic Acid and Enzyme*, vol. 46, No. 15, pp. 2154-2162, Dec. 2001. (English Summary).
Sugiyama et al., "Production of recombinant SERA proteins of *Plasmodium falciparum* in *Escherichia coli* by using synthetic genes", *Vaccine*, vol. 14, No. 11, pp. 1069-1076, 1996.
Morimatsu et al., "Sequence diversity in the amino-terminal 47 kDa fragment of the *Plasmodium falciparum* serine repeat antigen", *Molecular and Biochemical Parasitology*, vol. 86, pp. 249-254, 1997.
Fox et al., "*Plasmodium falciparum*: An Epitope within a Highly Conserved Region of the 47-kDa Amino-Terminal Domain of the Serine Repeat Antigen Is a Target of Parasite-Inhibitory Antibodies", *Experimental Parasitology* 85, Article No. PR964118, pp. 121-134, 1997.
Sano et al., "Purification and characterization of dihydrofolate reductase of *Plasmodium falciparum* expressed by a synthetic gene in *Escherichia coli*", *Molecular and Biochemical Parasitology*, vol. 63, pp. 265-273, 1994.
Suzue et al., "Protective immunity induced in squirrel monkeys with recombinant serine repeat antigen (SERA) of *Plasmodium falciparum*", *Parasitology International*, vol. 46, pp. 17-25, 1997.
Knapp et al., "A new blood stage antigen of *Plasmodium falciparum* highly homologous to the serine-stretch protein SERP", *Molecular and Biochemical Parasitology*, vol. 44, pp. 1-14, 1991.
Belperron et al., "Immune Responses Induced by Gene Gun or Intramuscular Injection of DNA Vaccines That Express Immunogenic Regions of the Serine Repeat Antigen from *Plasmodium falciparum*", *Infection and Immunity*, vol. 67, No. 10, pp. 5163-5169, 1999.
Pang et al., "Antibodies Reactive with the N-terminal Domain of *Plasmodium falciparum* Serine Repeat Antigen Inhibit Cell Proliferation by Agglutinating Merozoites and Schizonts", *Infection and Immunity*, vol. 67 No. 4, pp. 1821-1827, 1999.
*Molecular Biology of the Cell*, vol. 7, pp. 1485-1498, 1996.

* cited by examiner

*Primary Examiner*—Robert A. Zeman
*Assistant Examiner*—Lakia J Tongue
(74) *Attorney, Agent, or Firm*—Wenderoth, Lind & Ponack, L.L.P.

(57) ABSTRACT

The present invention provides a polypeptide SE36 derived from the N-terminal domain (47 kd) of SERA (serine-repeat antigen) produced by malaria parasite, *Plasonodium falciparum*, at the erythrocyte stage, a process for purifying said polypeptide, and a malaria vaccine and diagnostic agent using as an active component said purified antigen obtained therefrom. SE36 can be produced in *Escherichia coli* on a large scale by deleting all or part of polymerized serines of the 47 kd serine-repeat region, whereby high purification is permitted. The human IgG3 antibodies specifically binding to SE36 prevents highly effectively growth of the protozoa in the red blood cells to inhibit fever and cerebral malaria, and further prevent the death.

2 Claims, 8 Drawing Sheets

Fig. 1

```
              16           33    34                     57
Hond-1   NKNVIKCTGESQTGNTGG————GQAGNTVGDQAGSTGGSPQGSTGA————
[SE36]   M··················                 ················        ————
         [1]          [18]  [19]                  [42]

58                                              111
Hond-1   ————SQPGSSEPSNPVSSGHSVSTVSVSQTSTSSEKQDTIQVKSALLKDYMGLKVTGP
[SE36]   ————·······································································
             [43]                                           [96]

112         125         143                         171
Hond-1   CNENFIMFLVPHIYIDVDTEDTNIELRTTLKETNNAISFESNSGSLEKKKYVKLPSNGTT
[SE36]   ·······························································
          [97]        [110]       [128]

172  178       190·191                        226  231
Hond-1   GEQGSSTGTVRGDTEPISDSSSSSSSSSSSSSSSSSSSSSSSSSSSSSSSSSSSSSSESLPAN
[SE36]   ·················                                          ······
          [157] [163]       [175]                                [178]

232      242                267                    291
Hond-1   GPDSPTVKPPRNLQNICETGKNFKLVVYIKENTLIIKWKVYGETKDTTENNKVDVRKYLI
[SE36]   ·······························································
          [184]     [194]              [219]

292     300              321                        351
Hond-1   NEKETPFTSILIHAYKEHNGTNLIESKNYALGSDIPEKCDTLASNCFLSGNFNIEKCFQC
[SE36]   ·······························································
          [244]    [252]              [273]

352          375    382
Hond-1   ALLVEKENKNDVCYKYLSEDIVSNFKEIKAE
[SE36]   ························
          [304]        [327]  [334]
```

Fig. 2

```
MKNVIKCTGESQTGNTGGGQAGNTVGDQAGSTGGSPQGSTGASQPGSSEPSNPVSSGHSV     60
STVSVSQTSTSSEKQDTIQVKSALLKDYMGLKVTGPCNENFIMFLVPHIYIDVDTEDTNI    120
ELRTTLKETNNAISFESNSGSLEKKKYVKLPSNGTTGEQGSSTGTVRGDTEPISDSSESL    180
PANGPDSPTVKPPRNLQNICETGKNFKLVVYIKENTLIIKWKVYGETKDTTENNKVDVRK    240
YLINEKETPFTSILIHAYKEHNGTNLIESKNYALGSDIPEKCDTLASNCFLSGNFNIEKC    300
FQCALLVEKENKNDVCYKYLSEDIVSNFKEIKAE                             334
```

Fig. 3

```
             16           33 34                    57
Hond-1  NKNVIKCTGESQTGNTGG————————GQAGNTVGDQAGSTGGSPQGSTGA————
HB3     ·············GQAGNTGG····················————
3D7     ·················——————————————·········SPQGSTGASP
T9/102  ·················V································
K1      ·················V·V······························
[SE36]  M················——·······························
        [1]              [18] [19]                 [42]

58                                              111
Hond-1  ————SQPGSSEPSNPVSSGHSVSTVSVSQTSTSSEKQDTIQVKSALLKDYMGLKVTGP
HB3     ————··················································
3D7     QGSTGA················································
[SE36]     [43]                                             [96]

112     125           143                          171
Hond-1  CNENFIMFLVPHIYIDVDTEDTNIELRTTLKETNNAISFESNSGSLEKKKYVKLPSNGTT
HB3     ············································................
3D7     ····························K······························
[SE36]  [97]    [110]         [128]

172 178    190                              226 231
Hond-1  GEQGSSTGTVRGDTEPISDSSSSSSSSSSSSSSSSSSSSSSSSSSSSSSSSSSSESLPAN
HB3     ···S···——————········N·········································
K1      S······——————···················——————————VNP···
Camp    ·········S······································——————————VNP···
3D7     ················································
T9/96   ·······························——————————
[SE36]  ····························——————··············
        [157] [163]  [175]                           [178]

232       242              267                  291
Hond-1  GPDSPTVKPPRNLQNICETGKNFKLVVYIKENTLIIKWKVYGETKDTTENNKVDVRKYLI
HB3     ············································
K1      ·AG·TPDAKKK·································
PA/7    ·AG·TPDAKKK·····················L···········
3D7     ································L···········
[SE36]  [184]    [194]             [219]

292    300                321                      351
Hond-1  NEKETPFTSILIHAYKEHNGTNLIESKNYALGSDIPEKCDTLASNCFLSGNFNIEKCFQC
HB3     ············································
T9/102  ·······N·············S······························
PA/7    ·······N·············I······························
3D7     ·······N·············I······························
[SE36]  [244]  [252]             [273]

352          375    382
Hond-1  ALLVEKENKNDVCYKYLSEDIVSNFKEIKAE
HB3     ·······················K······
3D7     ······························
[SE36]  [304]        [327]  [334]
```

ANTIGENIC POLYPEPTIDE SE36 OF MALARIA PLASMODIUM, PROCESS FOR PURIFICATION THEREOF, AND VACCINE AND DIAGNOSTIC AGENT USING THE ANTIGEN

This application is a continuation of Ser. No. 10/239,517, filed Oct. 29, 2002, now abandoned, which is a 371 U.S. national stage of International Application No. PCT/JP02/00506 filed Jan. 24, 2002.

TECHNICAL FIELD

The present invention relates to an antigenic polypeptide derived from SERA (serine-repeat antigen) of *Plasmodium falciparum*, to a process for purification of the polypeptide, and to malaria vaccine and diagnostic agent using as an active component the purified antigen obtained from the above method.

BACKGROUND ART

Malaria is caused by infection of one or more of malaria protozoa (*Plasmodium*), including the following known 4 species: *falciparum* malaria (*Plasmodium falciparum*; hereinafter abbreviated to as "Pf"), *vivax* malaria (*P. uivax*), *malariae* malaria (*P. malariae*) and *ovale* malaria (*P. ouale*). The above-described protozoa in a form of sporozoite invade and infect a human body from the salivary gland of a female malaria-carrying mosquito (*Anopheles*) through the bite. An outline of the life cycle of the parasite is as follows:

[Mosquito] formation of sporozoites by sexual growth of the protozoa→<bite>→[Human] sporozoite<invasion into the blood>→<invasion into the hepatocyte>→[Exo-erythrocyte stage] sporozoite in the hepatocyte→schizont→formation of a merozoite and release into the blood by destruction of the hepatocytes→<invasion of the merozoite into the erythrocyte>

→[Intra-erythrocyte stage] merozoite→ring→trophozoite→asexual growth of the schizont→repetition the cycle of the formation of the merozoite and release into the blood by destruction of the erythrocytes→<crisis>; or merozoite→differentiation into male and female gametocytes→<hematophagia>→

[Mosquito] male and female gametocytes→male and female gametes→sexual reproduction→differentiation into ookinetes→differentiation into oocytes and growth→formation of the sporozoite and moving to the salivary gland.

With respect to antigens of the above-described malaria parasite (Pf) relating to the invention, it has been reported that there are various antigens as many as 40 species in total as shown below. For example, at the above-described intra-erythrocyte stage in the life cycle, the followings are exemplified: SERA (serine-repeat antigen; another called, SERP: serine-rich protein), HRP-2 (histidine-rich protein 2), etc.; in the merozoite, MSP-1 (merozoite surface antigen-1), MSP-2 (merozoit surface antigen-2), AMA-1 (apical membrane antigen-1), etc.; in the sporozoite and also at the exo-erythrocyte stage, SSP-2 (sporozoite surface antigen-1), LSA-3 (liver-specific antigen-3), etc.; and at the sexual stage, Pfs 230, Pfs 45/48, etc. ("Topley & Wilson's Microbiology and Microbial Infections", 9th edition, volume 5, Parasitology, p. 383, L. Collier, et al., published by Arnold Co., 1998). It has energetically been attempted to develop the vaccine using an antigen alone or as a mixture or in a form of a gene DNA, though no practically usable vaccine has been known ("The Jordan Report 2000", pp 141-142, US National Institute of Health, published in 2000).

Moreover, the so far known techniques for producing malaria vaccines using the above-described SERA (or SERP) and a gene thereof relating to the invention have been described, for example, in European Patent EP 283,882 (the 1882-1917th bases, the 2403-2602nd bases, and the 2602-2631st bases of a 140 kd antigenic gene in SERP encode hydrophilic epitopes), U.S. Pat. No. 5,395,614 (a fusion protein of SERP epitope and HRP-2), U.S. Pat. No. 6,024,966 (a gene which can be identified by two species of probes A and B encodes SERA antigenic polypeptide), and a report (Vaccine, 14, pp. 1069-1076, 1996) relating to the expression system of SE47' derived from the 47 kd SERA and production of the SE47' antigen in this system. However, the antigenicity and purity of these vaccine antigens are insufficient, and the purification process is not suitable to mass production. Further, their safety, efficacy or homogeneity is not clearly assured, and therefore remarkable originality and progress are necessitated in the production process for solving these problems. Reduction to practice has not yet been achieved for these antigens, accordingly.

On the other hand, SERA (serine-repeat antigen) is a protein antigen of 115 kd in molecular weight consisting of 989 amino acids in total and expressed by Pf gene at the intra-erythrocyte stage. The structure of SERA consists of 3 domains, i.e., 47 kd-50 kd-18 kd, in order of the N-terminal to the C-terminal direction. SERA working as a precursor for these domains is expressed by 4 exons distributed on the SERA gene DNA comprising 5868 bases in total, and then processed and cleaved at the intra-erythrocyte stage during release of the merozoite to yield the above-described 3 domains. (Molecular and Biochemical Parasitology, 86, pp. 249-254, 1997; and Experimental Parasitology, 85, pp. 121-134, 1997). In this connection, the full-length data of the SERA gene DNA and which encoded the amino acid sequence are open to public and available from GenBank (Accession Number: J0400; www.ncbi.nlm.nih.gov). The N-terminal region of SERA (hereinafter referred to as "47 kd domain") consists of 382 amino acids in total. The homology search between the Pf strains relative to the sequence indicates that SERA is varied since there are in some regions deletion or addition of an amino acid or acids and about 20 variation of amino acids (non-synonymous substitution) (Molecular and Biochemical Parasitology, supra; and Experimental Parasitology, supra).

Malaria is an infectious disease occurring in many places in the world, ranking after acute lower respiratory tract infections, AIDS, and diarrhea. According to the estimation by WHO (World Health Organization), the number of patients suffering from malaria was approximately 45 million in 1999, among which approximately 1.1 million were killed (The World Health Report 2000, p. 164 and p. 170, published by WHO in 2000). Such a high rate of death is attributed to severe *falciparum* malaria, namely, cerebral malaria. The major cause is considered as cerebral thrombosis induced by accumulation of destructed erythrocyte debris accompanied by the Pf growth, and this results in death through sensory paralysis, delirious talk, dystrophy, convulsion, etc. It is no exaggeration to say that avoidance of such cerebral malaria is the most important problem to be solved.

As a reason of frequent occurrence of malaria, it has been proposed that drug-resistant strains or multiple drug-resistant strains of malaria parasite against anti-malaria drugs such as quinine, chloroquine, pyrimethamine-sulfadoxine, mefloquine, halofantrine, etc. have emerged and spread. Since the end of 1950s at which time occurrence of chloroquine-resistant Pf was reported in South America and Southeast Asia, such resistant parasite have spread through the almost whole area of malaria-occurring tropical or subtropical zones except a part of Central America, the Caribbean Sea, and the Middle and Near East. Therefore, the control of malaria has become currently global problems to be solved in the health administration with rapidly increased diplomatic relations so that it was inevitably recommended to spread DDT as an emergency measure (WHO Expert Committee on Malaria: Technical Report Series, No. 892, pp. 1-71, 2000, published by WHO).

Additionally, a future feared problem is the expansion of malaria-occurring areas accompanied by global warming (Science, 289, 1763-1766, 2000). Now, it is an imminent and urgent problem to provide measures against malaria for the whole humankind.

In particular, in development of a malaria vaccine, though a great deal of effort and energy has been made to develop the vaccine all over the world, no effective vaccine has been provided. The main reason is considered to be the following problems (a) to (c): (a) Since the malaria antigens are various as mentioned above, it is difficult and obscure to identify a protective antigen from such various antigens; (b) Malaria antigens are of polymorphic gene, and the antigenicity is variable depending on the strain of Pf parasite. Therefore, a single antigen derived from Pf, for example, a well-known antigen as a candidate for vaccines such as MSP-1, AMA-1, etc., has a very narrow antigenic spectrum, so that it is not necessarily effective for prevention from infection by any species of Pf strains; and (c) The antigens as a candidate for vaccines such as MSP-1, AMA-1, etc., as well known, is denatured during purification, and destructed in its steric structure or epitope to decrease or lose its antigenicity.

DISCLOSURE OF INVENTION

The invention provides a protein antigen (polypeptide SE36) derived from SERA of *falciparum* malaria parasite Pf, a synthetic polynucleotide which encodes polypeptide SE36, a process for purification of polypeptide SE36, and a malaria vaccine and a diagnostic agent using as an active component said purified antigen obtained from the above process. Thus, the above problems can be solved.

In this connection, it is noted that the invention is based on the following findings corresponding to the above-described problems (a) to (c):

(a) The antibody titer of IgG3 for the SE36 antigen of the invention surprisingly correlates almost completely with the acquired immunity against malaria of the inhabitants in a malaria-prevalent area. The above-described IgG3 antibody existing in the sera of such local residents inhibit the growth of Pf in the erythrocytes (the inhibition of Pf growth results in inhibition of fever and destruction of the erythrocytes caused by malaria infection, and further death by cerebral malaria is prevented).

(b) This SE36 antigen has a broad antigenic spectrum and functions as a common antigen for the typical types of genetic polymorphism appearing in SERA47 kd domain, i.e., the following 3 strains: FCR3, Honduras-1, and K1 (Molecular and Biochemical Parasitology, supra). The above-described IgG3 antibody inhibits growth of those whole types of Pf parasite based on neutralization reaction.

(c) A method for purification of SE36 antigen produced in mass production was found, by which the antigenicity or epitope of SE36 antigen is not destroyed or destructed.

On the basis of the above-described findings, the following inventions (1) to (15) are provided.

(1) A polypeptide SE36 consisting of the full length of the amino acid sequence of SEQ ID NO: 4.

(2) The polypeptide SE36 of invention (1), which has at least one of the following amino acid substitution in the amino acid sequence of SEQ ID NO: 4:
the 19th Gly is Val;
the 128th Glu is Lys;
the 157th Gly is Ser;
the 160th Gly is Ser;
the 172nd Pro is Ser;
the 178th Glu is Val;
the 179th Ser is Asn;
the 180th Leu is Pro;
the 185th Pro is Ala;
the 186th Asp is Gly;
the 188th Pro is Thr;
the 189th Thr is Pro;
the 190th Val is Asp;
the 191st Lys is Ala;
the 192nd Pro is Lys;
the 193rd Pro is Lys;
the 194th Arg is Lys;
the 219th Ile is Leu;
the 252nd Ser is Asn;
the 273rd Ala is Ser;
the 274th Leu is Ile; and
the 327th Asn is Lys.

(3) The polypeptide SE36 of invention (1) or (2), wherein which an oligopeptide consisting of the amino acid sequence of SEQ ID NO: 5 or SEQ ID NO: 6 is added between the 18th Gly and the 19th Gly in the amino acid sequence of SEQ ID NO: 4.

(4) The polypeptide SE36 of invention (1) or (2), wherein an oligopeptide consisting of the amino acid sequence of SEQ ID NO: 7 or SEQ ID NO: 8 is added between the 42nd Ala and the 43rd Ser in the amino acid sequence of SEQ ID NO: 4.

(5) The polypeptide SE36 of invention (1) or (2), wherein an oligopeptide consisting of the amino acid sequence of SEQ ID NO: 5 or SEQ ID NO: 6 is added between the 18th Gly and the 19th Gly in the amino acid sequence of SEQ ID NO: 4, and an oligopeptide consisting of the amino acid sequence of SEQ ID NO: 7 or SEQ ID NO: 8 is added between the 42nd Ala and the 43rd Ser in the amino acid sequence of SEQ ID NO: 4.

(6) The polypeptide SE36 of any one of inventions (1) to (5), wherein an oligopeptide consisting of the amino acid sequence of from the 19th Gly to the 26th Gly in the amino acid sequence of SEQ ID NO: 4 is deleted.

(7) The polypeptide SE36 of any one of inventions (1) to (5), wherein an oligopeptide consisting of the amino acid sequence of from the 163rd Thr to the 175th Asp in the amino acid sequence of SEQ ID NO: 4 is deleted.

(8) The polypeptide SE36 of any one of inventions (1) to (5), wherein an oligopeptide consisting of the amino acid sequence of the 19th Gly to the 26th Gly in the amino acid sequence of SEQ ID NO: 4 is deleted, and an oligopeptide consisting of the amino acid sequence of the 163rd Thr to the 175th Asp in the amino acid sequence of SEQ ID NO: 4 is deleted.

(9) The polypeptide SE36 of any one of inventions (1) to (8), wherein the number of serine residues polymerized through a peptide linkage between the 175th Asp and the 178th Glu in the amino acid sequence of SEQ ID NO: 4 is in the range of 0 to 10.

(10) A polypeptide which has an antigenicity crossing with the polypeptide SE36 of claim 1, and in which the number of the polymerized serine residue detected by the amino acid homology search is in the range of 0 to 10.

(11) A malaria vaccine, which comprises as an active component at least one of polypeptides selected from the group consisting of the polypeptides SE36 of inventions (1) to (9) and the polypeptide of invention (10).

(12) A diagnostic agent for malaria, which comprises as an active component at least one of polypeptides selected from the group consisting of the polypeptides SE36 of inventions (1) to (9) and the polypeptide of invention (10).

(13) A synthetic DNA fragment encoding any one of the polypeptides SE36 of inventions (1) to (9).

(14) A process for purifying a polypeptide SE36, which comprises collecting of the cells from the culture solution of *Escherichia coli* transformed with the synthetic DNA fragment of invention (13), and carrying out each step in order of cell destruction, fractionation by salting-out, membrane filtration, column chromatography, hydrophobic chromatography, precipitation by salting-out, membrane filtration, column chromatography, and dialysis.

(15) The process of invention (14), wherein the dialysis is conducted after the concentration of the polypeptide SE36 is adjusted at 10 to 100 μg/ml.

BRIEF DESCRIPTION OF DRAWINGS

FIG. 1 shows the difference between the 16th to 382nd amino acid (N-E) sequence of the 47 kd SERA domain of *Plasmodium falciparum* Honduras-1 and the 1st to 334th amino acids (M-E) in the full length amino acid sequence of the polypeptide SE36. The sequence is described by the one-letter symbols of amino acids from the N-terminal to the C-terminal direction. Hond-1 means Honduras-1 strain, the dotted line, . . . . , means the same sequence, the solid line, - - - , means deletion, and [number] means the amino acid number of SE36, respectively.

FIG. 2 shows the full length of the amino acid sequence as the basic structure of the polypeptide SE36 molecule. The sequence is described by the one-letter symbols of amino acids from the N-terminal to the C-terminal direction.

FIG. 3 shows the difference of the 47 kd amino acid sequence of Honduras-1 strain as described in FIG. 1 as a standard sequence from those of other *P. falciparum* strains. [Number] means the amino acid number of SE36.

In FIG. 9, "○" indicates the SE36 protein of the full length having a natural steric structure, "●" indicates an SE36 protein, and "■" indicates an SE50A protein having no vaccine effect, respectively.

BEST MODE FOR CARRYING OUT THE INVENTION

Figure 4:
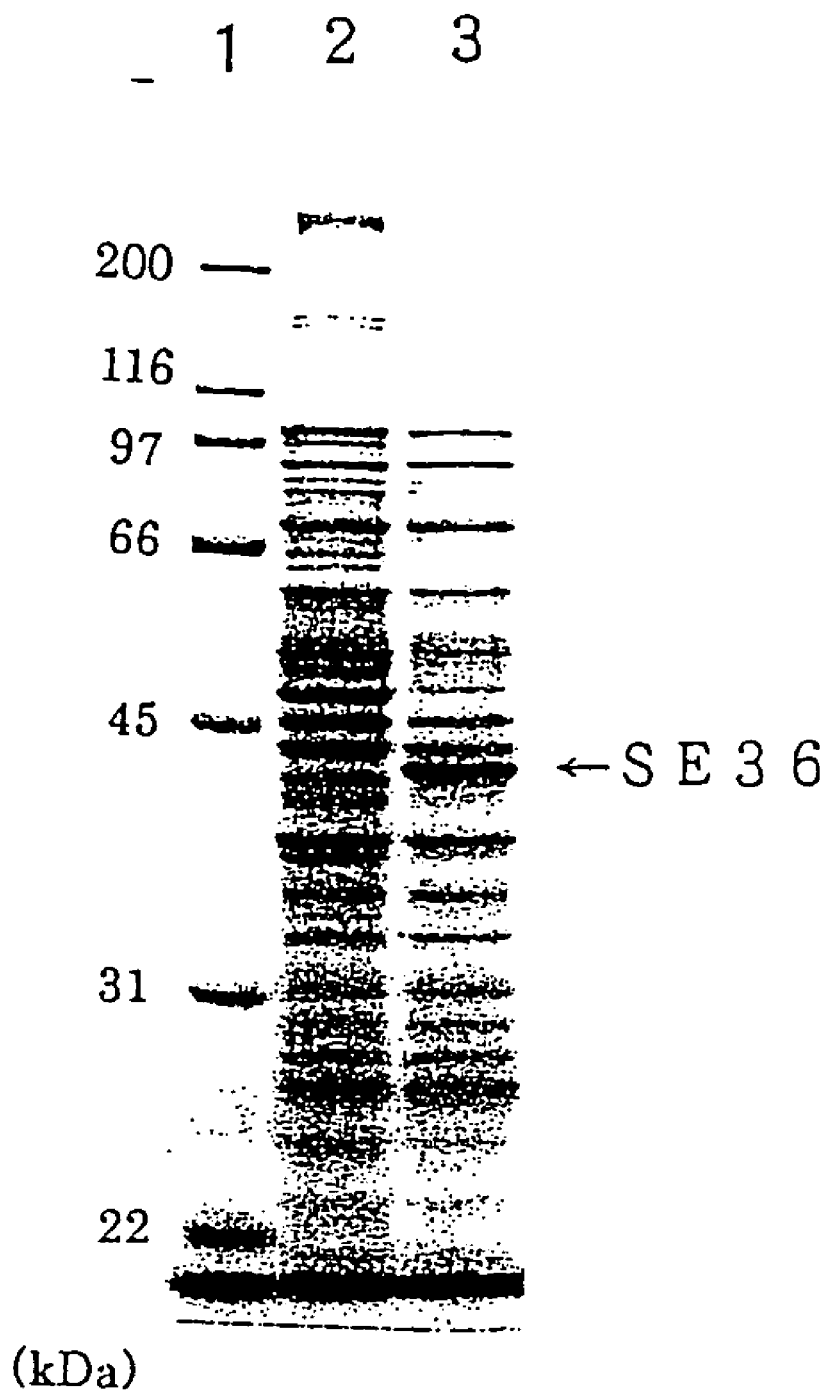
FIG. 4 shows a diagram of electrophoresis. The column 1 indicates a molecular maker, the column 2 does the whole proteins of *Escherichia coli* in which no SE36 has been expressed, and the column 3 does the whole proteins of *Escherichia coli* in which SE36 has been expressed with addition of IPTG.

Basic Structure of the Polypeptide SE36 Molecule:

The polypeptide SE36 (hereafter it is written as "SE36") of the invention is derived from SE47' antigen (Vaccine, 14, pp. 1069-1076, 1996; hereinafter abbreviated to as "SE47'") on the basis of SERA domain 47 kd (hereafter it is written as "47 kd") of the above-described Honduras-1 strain of *falciparum* malaria parasite Pf. SE 36 has the basic structure consisting of the full length or partially deleted sequence of serine-repeat region of 47' kd. FIG. 1 shows the difference between the amino acid sequences of the basic structure of SE36 and of the above 47' kd (Honduras-1 strain origin). FIG. 2 shows the full length of the amino acid sequence in the basic structure of SE36. In these figures, the amino acid sequence is described by the one-letter symbols of amino acids from the N-terminal to the C-terminal direction. In FIG. 1, Honduras-1 strain is abbreviated to Hond-1, the deleted region detected by the search for the homology between this strain and the other Pf strains is represented by the solid line, - - - , and the same amino acid sequence is represented by the dotted line, . . . . In FIG. 1, the basic structure of SE36 comprises a polypeptide consisting of 334 amino acids in total, in which the sequence starts from the N-terminal methionine (the 1st amino acid) of 382 amino acids constituting 47 kd of Hond-1, and in the ordinal number towards the C-terminal, the 16th amino acid codon (aspartic acid) is substituted with an initiation codon (methionine), and a translation stop codon is inserted after the 382nd amino acid (glutamic acid), and further the 33 polymerized serine residues (193rd to 225th serines) occupying the serine repeat region is deleted.

In the "Sequence Listing" contrasted with the above-described FIGS. 1 and 2, the "SEQ ID NO: 1" shows the full length of the 47 kd gene DNA base sequence of SERA domain of Honduras-1, and encoding the full length of the 47 kd amino acid sequence.

"SEQ ID NO: 2" shows the full length of the 47 kd amino acid sequence described in SEQ ID NO: 1. This sequence comprises 382 amino acids in total, wherein the 16th-382nd amino acids are the same as those of Hond-1 as shown in FIG. 1 and FIG. 3 as will be mentioned below.

"SEQ ID NO: 3" shows the full length of the synthetic DNA sequence of SE36 gene after conversion into a codon of *Escherichia coli* and encoding the full length of the amino acid sequence. This amino acid sequence having the 1st amino acid Met is derived from the above-described 47 kd by substitution of the 16th amino acid Asn with an initiation codon Met. In the base sequence, most of Pf codons are converted into the codons of *Escherichia coli*. Such conversion into the codons of *Escherichia coli* will be described below.

"SEQ ID NO: 4" shows the full length of the amino acid sequence as a basic structure of an SE36 molecule described in SEQ ID NO: 3. This sequence is the same as that of SE36 described in FIG. 1 and each amino acid sequence described in FIG. 2.

Derivatives and Mutants of SE36:

FIG. 3 indicates mutations in SE36. In FIG. 3, an amino acid sequence of a Honduras-1 strain (Hond-1) as shown in FIG. 1 is used as a standard, and the amino acid number is given in the same way as in FIG. 1. Deletion is indicated by the solid line, - - - , and the same sequence is indicated by the dotted line, . . . . Using this indication, respective amino acid sequences of other Pf strains (HB3, T9/96, 3D7, K1, T9/102, PA/7, and Camp) are described by arranging in lines with Hond-1 to show the difference between the amino acid sequences of these strains. In FIG. 3, mutation or difference between the above standard (Hond-1) and other strains in their amino acid sequences is indicated by one-letter symbols of amino acids.

Hereinafter, the constitution and embodiment of the SE36 derivatives or mutants are described on the basis of the position and region of amino acid mutation as described in FIG. 3 as well as an amino acid sequence of the SE36 basic structure as described in SEQ ID NO: 4 in Sequence Listing by matching FIG. 3 with SEQ ID NO: 4.

As shown in FIG. 2 (SEQ ID NO: 4), the basic structure of the SE36 molecule is a polypeptide consisting of 334 amino acids in total. Processing, changing or modifying of the basic structure affords its derivatives or processed, modified or mutated products. These may be prepared by utilizing alone or in proper combination non-synonymous substitution of the amino acids based on FIG. 3, addition or deletion of an oligopeptide, and limitation of the number of polymerized serine residues occupying the serine-repeat region, or selection of an 47 kd epitope (Experimental Parasitology, supra). According to the invention, the followings (1) to (4) are available.

(1) In the amino acid sequence of SEQ ID NO: 4, at least one of the following amino acid substitution is available:
  (a) 19th Gly is Val;
  (b) 128th Glu is Lys;
  (c) 157th Gly is Ser;
  (d) 160th Gly is Ser;
  (e) 172nd Pro is Ser;
  (f) 178th Glu is Val;
  (g) 179th Ser is Asn;
  (h) 180th Leu is Pro;
  (i) 185th Pro is Ala;
  (j) 186th Asp is Gly;
  (k) 188th Pro is Thr;
  (l) 189th Thr is Pro;
  (m) 190th Val is Asp;
  (n) 191st Lys is Ala;
  (o) 192nd Pro is Lys;
  (p) 193rd Pro is Lys;
  (q) 194th Arg is Lys;
  (r) 219th Ile is Leu;
  (s) 252nd Ser is Asn;
  (t) 273rd Ala is Ser;
  (u) 274th Leu is Ile; and
  (v) 327th Asn is Lys.

(2) Considering mutual addition or deletion between amino acid sequences of Pf strains described in FIG. 3, it is possible to conduct addition or deletion of an oligopeptide in combination of the followings (i) to (vi) in the SE36 amino acid sequence of SEQ ID NO: 4:
  (i) Addition of an oligopeptide consisting of the amino acid sequence of SEQ ID NO: 5 between 18th Gly and 19th Gly;
  (ii) Addition of an oligopeptide consisting of the amino acid sequence of SEQ ID NO: 6 between 18th Gly and 19th Gly;
  (iii) Addition of an oligopeptide consisting of the amino acid sequence of SEQ ID NO: 7 between 42nd Ala and 43rd Ser;
  (iv) Addition of an oligopeptide consisting of the amino acid sequence of SEQ ID NO: 8 between 42nd Ala and 43rd Ser;
  (v) Deletion of an oligopeptide consisting of the amino acid sequence from 19th Gly to 26th Gly;
  (vi) Deletion of an oligopeptide consisting of the amino acid sequence from 163rd Thr to 175th Asp.

(3) In the SE36 amino acid sequence as described in SEQ ID NO: 4, the number of the polymerized serine residues binding each other through a peptide bond between 175th Asp and 178th Glu is in a range of 0 to 30, preferably 0 to 20, more preferably up to 10, i.e., 0 to 10. The reason why the number of serine residues is limited is as follows. First, the present inventors have experienced that it is difficult to purify the above-described SE47' having 35 polymerized serine residues and they could not put it to practical use (Vaccine, supra). Second, It has surprisingly been found that, in the relationship between the number of the polymerized serine residues in the serine repeat region and the physical properties of SE36, water soluble or solubility and antigenicity or immunogenicity of SE36 are enhanced with decrease of the number of the polymerized serine residues in SE36". This phenomenon suggests that deletion of the polymerized serines might change the steric structure of the SE36 molecule to expose a hydrophilic region including its epitope. According to the invention, accordingly, it is an essential condition to limit the number of the polymerized serine residues in the serine repeat region in order to facilitate purification of SE36 by solubilization and enhance its function and quality as an antigen.

(4) By combining the above-mentioned limitation of the serine residue number with selective utilization of the 47 kd epitope, it is possible to prepare a polypeptide which has an antigenicity crossing with SE36, and in which the number of the polymerized serine residue detected by the search for amino acid homology is, for example, in the range of 0 to 10. In this invention, the above-described crossing of antigenicity can be detected by an antigen-antibody reaction, and the serine repeat region may be detected by the search for amino acid homology using as a reference standard the amino acid sequence from 157th Gly to 183rd Asn of SE36 (SEQ ID NO; 4).

In other words, the above fact indicates that the amino acid sequence of SE36 as described in SEQ ID NO: 4 can be diversely modified, changed or processed in its molecular structure unless its antigenicity, immunogenicity and their spectra are damaged. Therefore, the polypeptide SE36 of the invention is a generic name including not only the SE36 basic structure as described in SEQ ID NO: 4 but also the above-mentioned derivatives or processed, mutated or modified products by addition, deletion or substitution of an amino acid or oligopeptide as described in (1)-(4). These products of SE36 may be used in vaccines or diagnostic agents, not only individually as the sole component but also as a mixture of at least two components in order to expand a spectrum of antigenicity or immunogenicity.

Moreover, it should be particularly noted that no fragment of naturally occurring 47 kd gene DNA encoding SE36 is used at all in production of SE36. According to the invention, mass production of SE36 may be achieved by synthesizing and cloning a DNA fragment (hereinafter sometimes referred to as SE36 gene DNA) encoding the full length of SE36 in a form of *Escherichia coli* codons which are converted from all naturally occurring Pf codons encoding the amino acid sequence, followed by construction of an expression vector for the synthesized gene clone, subsequent insertion of the vector into a host *Escherichia coli*, and incubation of the transformant thus prepared. The above-mentioned conversion into *Escherichia coli* codons to increase expression efficiency of SE36 gene DNA in *Escherichia coli* is conducted in view of industrial applicability intending mass production of SE36 because the efficiency with the native Pf codons in *Escherichia coli* is low.

Synthesis and Cloning of SE36 Genetic DNA:

An armchair-estimated base sequence of SE36 gene DNA of Pf and an amino acid sequence coded thereby are available from well-known publication organizations for gene data base, for example, DDBJ, GenBank, EMBL, etc., on the Internet.

Armchair conversion of Pf codons into *Escherichia coli* codons may be conducted referring to, for example, the Coden Usage database of GenBank or the inventor's publications (the above-described Vaccine; and Molecular Biochemistry of Parasitology, 63, 265-273, 1994). In the conversion into *Escherichia coli* codons, it should be noted to consider the native amino acid sequence of naturally occurring Pf as important and to avoid damage of its antigenicity due to non-synonymous substitution of amino acids, except substitution of the N-terminal amino acid with an initiation codon Met.

In syntheses of DNA, a commercially available DNA synthesizer, e.g., DNA/RNA synthesizer [Applied Biosystem Model 392: PE Co., USA] may be utilized. By such a synthesizer, sense (+) and antisense (−) DNA fragments in which about 100 to about 200 nucleotides are polymerized, are synthesized, respectively, and each DNA fragment thus synthesized is purified, for example, by polyacrylamide electrophoresis. Then, a complementary strand (pair) of the purified single-stranded DNA fragment is annealed to give a synthetic double-stranded DNA fragment.

In cloning of the synthetic double-stranded DNA fragment, a known or commercially available cloning vector of which the host is *Escherichia coli* (a great deal of vectors disclosed in "Cloning Vectors: A Laboratory Manual", I-1 to I-D-i-8, P. H. Pouwels, et al., Elsevier 1988), for example, a combination of a plasmid pBluescript II SK+ and *E. coli* XL1-BLue [Stratagene, USA] may be used. In such cloning, for example, a restriction enzyme-digested fragment of the above-described DNA fragment is inserted into the restriction enzyme sites of a vector digested with the same enzyme, and thus constructed vector is transferred to a host to give a transformant clone. Next, each clone containing the double-stranded DNA fragment is amplified by culture of the above transformant, and each base sequence can be determined by means of the chain terminator method (dideoxy method) or the Maxam-Gilbert method. In this procedure, a commercially available DNA sequencer, e.g., ABI PRISM 3700 [PE CO., USA], may be used. Based on the results, approximately 5 to 10 clones of double-stranded DNA fragments covering the full length of SE36 gene DNA is selected.

The cloning of the full length of SE36 gene DNA may be achieved by ligating the above-described double-stranded DNA fragments together. For example, when 8 clones (8 pairs) are obtained in the above-described operation, these double-stranded DNA fragments can be ligated one by one to give the full length of SE36 gene DNA. Then, the full length of DNA is cloned in the same manner as mentioned above. In carrying out the ligation, it is desirous to introduce a cohesive site for ligation by restriction enzymes at the both ends of each fragment of the double-stranded DNAs. In such introduction, the base sequence as codons has to be adjusted, so that the amino acid sequence of the native Pf is not changed.

Construction of an Expression System of SE36 Gene:

In producing an expression vector for SE36 gene, a known or commercially available expression vector of which the host is *Escherichia coli* (diversely disclosed in "Cloning Vectors: A Laboratory Manual"; supra), for example, a combination of plasmid pET-3a and *Escherichia coli* BL21 (DL3) pLysS or *Escherichia coli* BL21 (DL3) pLysE [Stratagene, USA] may be used. In producing such a vector, for example, a restriction enzyme-digested fragment containing the full length of SE36 gene DNA cut out from the above cloning vector is inserted into the restriction enzyme sites of a vector cleaved with the same enzymes. Alternatively, it may be prepared from pET-SE47' (Vaccine, supra). In this case, for example, the whole or partial region which encoding the serine repeat region is cut out from pET-SE47' or an SE47' synthetic gene containing it in the same manner as mentioned above. Then, the resulting expression vector is transferred to a host to give a transformant. From such transformants, the most appropriate one as an expression system for mass production of the polypetide SE36 can be screened in view of industrial applicability.

Production of Polypeptide SE36:

Mass production of SE36 is achieved by culturing the above-described transformant of *Escherichia coli*. In view of enhancement of productivity of SE36, in such culture, it is possible to improve or reform a manipulation such as use of an inducers, e.g., IPTG (isopropyl-1-thio-β-D-galactopyranoside), avoidance of catabolite repression, culture medium, culture temperature and period, removal of proteases in host cells, and the like. These may be achieved by alteration of an expression vector, and further by change of a promoter or host organism.

Purification of Polypeptide SE36:

When SE36 is secreted outside cells, a culture solution after removal of the cells from the above-mentioned transformant culture is used as a starting material for extraction. When SE36 is accumulated in the cells, the cells may be recovered from a culture, for example, by centrifugation, filtration, etc., and extracted to give the above-described SE36. At the first step of extraction, the cells may be destroyed by digestion with an enzyme, destruction with osmotic pressure, sudden pressure and decompression, sonication, use of various homogenizers, etc. The destroyed cells are then fractionated by a physical means, e.g., low speed centrifugation, ultra-centrifugation, filtration, molecular sieve, membrane concentration, etc., or a chemical means, e.g., precipitating agent, solubilizing agent, adsorbent and desorption agent, dispersing agent, etc., or a physicochemical means, e.g., electrophoresis, column chromatography, support, dialysis, salting-out, etc. These techniques may be used in combination. In applying these techniques, it is possible to properly choose a physicochemical condition such as temperature, pressure, pH, ion strength, etc.

In the invention, among the above-described various means and conditions, sonication, salting-out with ammonium sulfate, centrifugation, column chromatography, filtration, membrane concentration, etc. are used in combination in order of the following purification steps (1) to (10) to purify the SE36 polypeptide:

(1) Destruction of a cultured cell paste by sonication and removal of cell debris by centrifugation;

(2) Fractionation by salting-out with ammonium sulfate, wherein ammonium sulfate is added at a saturation of lower limit 20% and upper limit 50%, preferably at lower limit 30% and upper limit 35%, into water at 4° C.
(3) Solubilization of the SE36 polypeptide with a buffer solution which contains 6M to fully saturated urea, preferably 9M urea, 0.2% (w/w) to 5% (w/w) Tween 80, preferably 1% (w/w) Tween 80, and 2-mercaptoethanol or dithiothreitol or a reducing agent in a sufficient concentration for reduction of a disulfide bond;
(4) Fractionation by molecular weight by column chromatography using Sephacryl S-300 or S-200 or a corresponding molecular sieve together with a buffer solution containing 6M to fully saturated urea, preferably 9M urea, and 2-mercaptoethanol or dithiothreitol or a reducing agent in a sufficient concentration for reduction of a disulfide bond;
(5) Fractionation and dialysis conducted by hydrophobic column chromatography using Octyl Sepharose;
(6) Salting-out by 35-65% saturated ammonium sulfate, preferably 45-55% saturated ammonium sulfate;
(7) Solubilization of an SE36 polypeptide with a buffer solution which contains from 6M to fully saturated urea, preferably 9M urea, and 2-mercaptoethanol or dithiothreitol or a reducing agent in a sufficient concentration for reduction of a disulfide bond;
(8) Fractionation by molecular weight by column chromatography using Sephacryl S-300 or S-200 or a corresponding molecular sieve together with a buffer solution containing 6M to fully saturated urea, preferably 9M urea, and 2-mercaptoethanol or dithiothreitol or a reducing agent in a sufficient concentration for reduction of a disulfide bond;
(9) Fractionation by molecular weight by column chromatography using Sephacryl S-300 or S-200 or a corresponding molecular sieve;
(10) Dialysis following adjustment of the concentration of the SE36 protein at 10-100 μg/ml, preferably 20-30 μg/ml;
(11) Membrane concentration. In this connection, sterilization for preparation of vaccines may be carried out, for example, by filtration through a 0.22 μM-filter under sterilization.

Confirmation of SE36 Molecule and its Antigenicity:

Detection and size confirmation of an SE36 molecule may be achieved, for example, by determination of sedimentation coefficient, molecular sieve, SDS-polyacrylamide electrophoresis, etc. Antigenicity of the SE36 molecule may be confirmed by means of an antigen-antibody reaction using a polyclonal or monoclonal antibody to SERA 47 kd, for example, Western blot analysis, ELISA, agglutination reaction, fluorescent antibody technique, radioimmunoassay, and the like. In addition, immunogenicity of the SE36 polypeptide and the potency of an anti-SE36 antibody inhibiting growth of Pf parasite may be confirmed by means of the above-described antigen-antibody reaction using the serum of a patient suffering from *falciparum* malaria or an experimental small animal immunized with said polypeptide, e.g., rat, mouse, or by a blocking test for growth (i.e., neutralization reaction) of Pf merozoites within erythrocytes, determination of the blood Pf number in an anti-SE36 antibody carrier, and the like.

Preparation of Vaccines:

The above-purified polypeptide SE36 as an antigen is suspended in a solvent, e.g., isotonic PBS (phosphate buffer saline) to give a stock solution for vaccine.

In this connection, the above antigen for vaccine may be immobilized with a conventional inactivating agent to stabilize the steric structure. The inactivating agent includes, for example, formalin, phenol, glutaric dialdehyde, β-propiolactone, and the like, which may be added before or after preparation of the stock solution for vaccine. When formalin is used, the amount to be added is about 0.005 to 0.1% (v/v), the inactivation temperature is about 4 to 38° C., and the inactivation period is about 5 to 180 days. When the antigenicity is damaged by inactivation, it is necessary to add an original idea to moderate the inactivation condition. Such moderation may be achieved, for example, by reduction of an inactivating agent, addition of a neutral or basic amino acid, lowering of the inactivation temperature, etc. Free formaldehyde remaining unchanged after the inactivation step, if required, may be neutralized with addition of an equivalent of sodium hydrogen sulfite or removed by dialysis.

The above-described SE36 may be processed or modified in order to induce mucous or local immunity by oral or nasal inoculation of a vaccine. For that purpose, a technique of DDS (drug delivery system) using, for example, liposome, emulsion, microcapsules, micro-spheres, polylactic acid, polyglycolic acid, etc., may be applied. Thus resulting preparation is used as a stock solution for vaccine in the subsequent step.

The above stock solution for vaccine is diluted, for example, with the above-described PBS to adjust the amount of the antigen in the vaccine, so that antibody production is induced and immunity appears. In such a case, it is possible to add a stabilizer for increasing heat-resistance of vaccine, and an adjuvant as an auxiliary for enhancing antigenicity. As a stabilizer, for example, sugars or amino acids may be utilized, and as an adjuvant, mineral oil, vegetable oil, alum, aluminum compounds, bentonite, silica, muramyl dipeptide derivatives, thymosin, interleukin, etc., may be utilized.

Subsequently, the resulting vaccine is distributed in vials of proper volume, e.g., about 1 to 20 ml volume, and the vials are tightly closed or sealed to use as vaccine preparations. Such vaccine preparations may be used as liquid preparations or as dry preparations formed by lyophilization after distribution.

Assay of Vaccines:

Assay of vaccines relating to control on production processes or control of quality is conducted in accordance with the Japanese Rules (Minimum Requirement for Biological Products) based on Pharmaceutical Affairs Law (Law No. 145 enacted on 1960), Article 42, Section 1; recommendation by WHO, "Requirements for Biological Substances" [WHO Technical Report Series (TRS), No. 889, pp. 105-111, 1999], etc. Malaria vaccine has not yet been put to practical use, and there is no standard for pharmaceutical preparations. The assay, accordingly, may be conducted in accordance with a standard for an analogous vaccine, for example, a variety of rules on safety and efficacy as described in the recommendation by WHO, "Requirements for Hepatitis B Vaccines Made by Recombinant DNA Techniques" (the above-described TRS, No. 786, 1898, and No. 889, 1999), "Requirements for Japanese Encephalitis Vaccine (Inactivated) for Human Use" (the above-described TRS, No. 771, 1988), etc. For example, the assay for sterilization, denial of abnormal toxicity, protein content, purity, hydrogen ion concentration, confirmation of antigens, antigenic polypeptides, and the like may be conducted in accordance with the rules for a variety of required or recommended tests. The product lot that has get through all of the above tests may be put to practical use as a competent malaria vaccine preparation.

How to Use the Vaccine:

Inoculation of the vaccine is subcutaneously made, for example, at a dose of about 0.25 to 0.5 ml. Such inoculation may be done 1 to 3 times at intervals of about 2 to 4 weeks. The usage of the vaccine, however, is not limited to the above examples.

Preparation of Diagnostic Agents:

SE36 polypeptides can be provided as antigens for diagnosis of malaria, for example, as antigens for precipitation reaction, agglutination reaction, neutralization reaction, fluorescent antibody technique, enzyme immunoassay, radioimmunoassay, and the like. The above-described polypeptides can be inoculated intraperitoneally, subcutaneously or intramuscularly to an animal, for example, rabbit, guinea pig, mouse, etc., to generate antibodies. Such antibodies can be isolated from their sera, and provided for use in detection of antigens in the above various diagnostic methods. The antigens and antibodies used in diagnosis of the invention may be diluted with a solvent, for example, the above-described PBS, so that the content of them in the diagnostic agent corresponds to the amount necessary for the antigen/antibody reaction.

EXAMPLES

The embodiment, constitution and effect of the invention will be explained specifically by means of examples and reference examples. These examples, however, are not intended to limit the inventions.

Example 1

Construction of SE36 Expression System

The DNA base sequence of the full length SE36 gene that had been armchair-converted from Pf codons to *Escherichia coli* codons was divided into 8 fragments. For each divided fragment, a sense (+) strand and an antisense (−) strand were synthesized to obtain 16 single stranded DNA fragments in total (8 pairs), which were annealed to give 8 pairs of double-stranded DNAs. These sequences were ligated each other to give the full length of SE36 gene, from which an expression vector was constructed. In this operation, the basic procedure for cloning and ligation of the synthetic DNA fragments were conducted in accordance with the method of Sambrook et al. (Molecular Cloning: A Laboratory Manual, 2nd edition, Cold Spring Harbor Laboratory Press, 1989).

The above respective single-stranded DNA fragments were synthesized using a DNA/RNA synthesizer "Applied Biosystem Model 392" [PE Co., USA]. These synthesized fragments were purified by electrophoresis on 10% (w/v) polyacrylamide (containing 50 mM Tris-borate salt, pH 8.3, 1 mM EDTA, and 8 M urea). Then, 20 p moles of the + and − complimentary strands of the purified DNA fragments, were respectively mixed, and heated in a buffer solution (20 µl of 20 mM Tris-HCl, pH 7.0, 50 mM NaCl, and 2 mM $MgCl_2$) at 85° C. for 5 minutes. Further, the complimentary regions of the above both strands were annealed by lowering the temperature to 55° C. at a rate of 5° C./5 minutes and then to 25° C. at a rate of 5° C./10 minutes using the Zymoreactor II [ATTO Co., Japan]. After termination of annealing, an equal amount of a buffer solution [20 mM Tris-HCl, pH 7.8, 10 mM $MgCl_2$, 5 mM dithiothreitol (DTT), 1 mM each of 4 species of nucleoside-5'-triphosphate (NTP), and 3 units of T4 DNA polymerase] was added, and the mixture was kept at 4° C. for 5 minutes, 25° C. for 5 minutes, and then at 37° C. for 120 minutes. Thus resulting double-stranded DNA fragments for construction of SE36 genes were respectively digested with restriction enzymes KpnI and BamHI, and then cloned and multiplied with pBluescript II SK+ and *Escherichia coli* XL1-Blue. The base sequences of the above DNA fragments in the respective clones were determined by the dideoxy method, and 8 clones covering the full length of SE36 genes were screened. The synthesized double-stranded DNA fragments of these 8 clones (8 pairs) were ligated to give the full length of double-stranded DNA of SE36 gene. In this operation, it was considered to use the base sequence by which the amino acid sequence of the native Pf was not altered, and the restriction enzyme sites for ligation were introduced to both ends of the respective pair DNAs. Subsequently, the full length of SE36 gene was cloned with pBluescript II SK+, and then transfected to *Escherichia coli* XL1-Blue for proliferation. The base sequence was determined by the dideoxy method. The results are shown in SEQ ID NO: 3 of Sequence Listing.

Subsequently, the fragments of the above clone digested with restriction enzymes NdeI and BamHI were inserted and ligated into the NdeI-BamHI cleavage sites of a plasmid pET-3a to construct the SE36 expression vector pET-SE36. This expression vector was transfected to *Escherichia coli* BL21 (DE3) pLysS to give a transformant, *Escherichia coli* BL21 (DE) pLysS/pET-SE37, which was designated as *Escherichia coli* BL/SE36.

Example 2

Expression and Purification of SE36

*Escherichia coli* BL/SE36 prepared in Example 1 was incubated on an LB medium [Bacto-trypton 1% (w/v), Bacto-yeast extract 0.5% (w/v), and NaCl 1% (w/v)] containing 50 µg/ml of ampicillin at 37° C. for 18 hours to give seeds. The seeds (50 ml) were inoculated on the above fresh LB medium (5 L) and incubated at 37° C. When the cell number reached $1 \times 10^8$/ml, IPTG (isopropyl-1-thio-β-D-galactopyranoside) was added at the final concentration of 50 µg/ml, and further incubated at 37° C. for 3 hours. After termination of the incubation, the mixture was centrifuged (5,000 rpm, 10 minutes) to collect the cells as 3.2 g of cell paste. The paste was suspended into 9.6 ml of an ice-cold lysis buffer solution (50 mM Tris-HCl, pH 8.0, and 1 mM EDTA). Then, the procedure (1) to (6) was conducted at 4° C. in order as described.

(1) Sonication

The above-described paste cells were treated with ultrasonic wave (19.5 kHz, 50 W) for 20 seconds 6 times to destroy. The supernatant after centrifugation (15,000 rpm, 30 minutes) was collected and placed in a 20 ml-volume beaker.

(2) Salting-out with Ammonium Sulfate (I)

Into the above supernatant placed in the beaker was added 2.37 g of $(NH_4)_2SO_4$ crystals with stirring at 35% saturation, and the mixture was further stirred for 30 minutes to salt-out. The mixture was then centrifuged (12,000 rpm, 10 minutes), the supernatant was discarded, and the precipitate was suspended into 9 ml of an ice-cold ammonium sulfate solution [the above-described lysis buffer solution containing 1.1 M $(NH_4)_2SO_4$] at 30% (w/w) ammonium sulfate saturation. The resulting suspension was centrifuged (12,000 rpm, 10 minutes) and the supernatant was discarded. The precipitate was suspended again into 8.8 ml of a lysis buffer solution [50 mM Tris-HCl (pH 8.0), 1 mM EDTA, 50 mM 2-mercaptoethanol, 9 M urea, and 1% (w/v) Tween 80] for recovery. The recovered suspension (4.4 ml, 1/2 volume) was heated at 60° C. for 10 minutes, then again ice-cooled and filtered through a 0.45 µm filter [Millipore, USA].

(3) Column Purification (I)

The above filtrate was chromatographed on a column of Sephacryl S-300 (26/60) equilibrated with a GF buffer solution [50 mM Tris-HCl (pH 8.0), 1 mM EDTA, 50 mM 2-mercaptoethanol, and 8M urea](3.5 ml/fraction; flow rate=0.3 ml/minute; 4° C.). Each of the fractions 22-43 was subjected to SDS-polyacrylamide electrophoreses, based on which migration pattern the fractions 32-37 containing a large amount of SE36 protein were pooled. The remaining resuspended solution (4.4 ml) was also worked up in the same manner as above. The fractions were combined with the above-fractionated pool and used in the subsequent operation (4).

(4) Column Purification (II)

The above-fractionated pool was kept at room temperature, to which was added $(NH_4)_2SO_4$ at a rate of 0.093 g/ml pool with stirring, so that the final concentration of ammonium sulfate became 0.7M. On the other hand, a 13 ml-volume aqueous column of Octyl Sepharose (Pharmacia Biotech) was equilibrated with 10-fold volume of HIC buffer solution [the above GF buffer solution containing 0.7M $(NH_4)_2SO_4$]. The above fractionated and ammonium sulfate-adjusted pool was poured onto the column at a rate of 0.5 ml/minute. The column was then eluted with the HIC buffer solution until the absorbance decreased, and then for confirmation the column was eluted with a GF buffer solution containing no $(NH_4)_2SO_4$ to elute the adsorbed components. The fractions not adsorbed on the column were placed in a bag for dialysis and dialyzed in 1 L of 20 mM Tris-HCl buffer solution (pH 8.0)(containing 1 mM EDTA) as an outside solution at 4° C. for 10 hours, during which time the outside solution was changed twice.

(5) Salting-out with Ammonium Sulfate (II)

The bag after completion of the dialysis was further dialyzed in 0.3 L of 50% (w/w) saturated $(NH_4)_2SO_4$ solution [containing 20 mM Tris-HCl (pH 8.0) and 1 mM EDTA] as an outside solution at 4° C. for 10 hours to give proteins as precipitate. The precipitate was collected by centrifugation (12,000 rpm, 10 minutes) and suspended into 2 ml of GF buffer solution.

(6) Column Purification (III)

Figure 5:
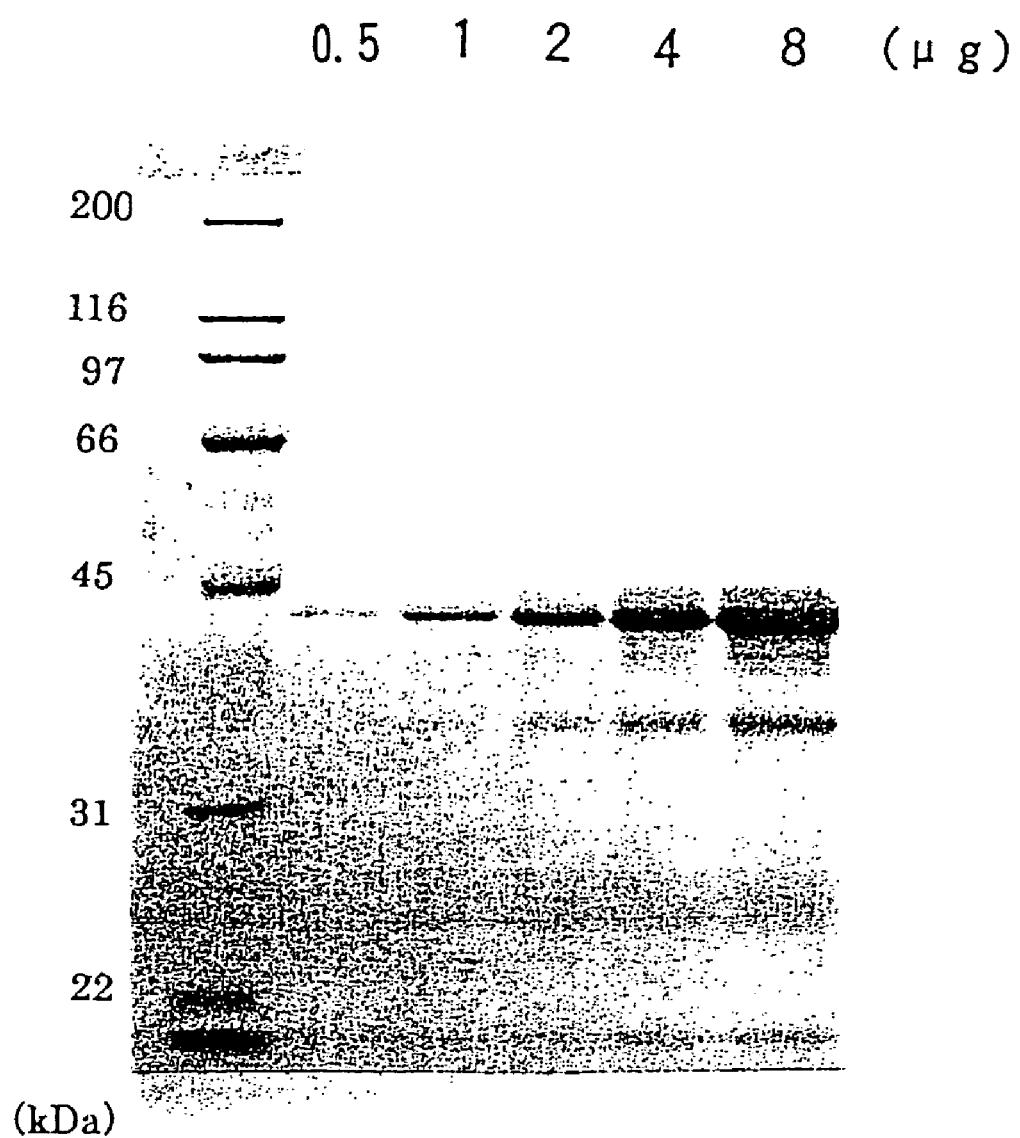
FIG. 5 shows a diagram of SDS-polyacrylamide electrophoresis of an SE36 sterile specimen (vaccine stock solution) prepared in Example 2. The diagram indicates that no contamination is detected visually other than SE36.

The above-prepared suspension was heated at 60° C. for 10 minutes and then cooled back to 4° C. This was filtered through a 0.45 μm-filter. The filtrate was chromatographed on a column of the above-described S-300 (26/60) equilibrated with a GF buffer solution 2 [10 mM Tris-HCl (pH 8.0), 1 mM EDTA, 20 mM 2-mercaptoethanol, and 8M urea] at a flow rate of 0.3 ml/minute. In the same manner as in the above item (3), each fraction was applied to SDS-polyacrylamide electrophoresis to screen fractions of the SE36 protein, which are gathered to give 12 ml of fraction. This fraction was added to a dilution buffer [10 mM Tris-HCl (pH 8.0), 1 mM EDTA, and 2M urea] with stirring so as to give a solution of the SE36 protein at a concentration of 25 μg/ml. The diluted solution was dialyzed in 2 L of PBS as an outside solution [9 mM $NaHPO_4$, 3 mM $NaH_2PO_4$, and 137 mM NaCl (pH 7.4)] at 4° C. for 10 hours. During this operation, the outside solution was changed twice. After dialysis, the inside solution was concentrated with Centprep 30, and filtered through a Durapore 0.22 μm-filter [Millipore, USA] for sterilization to give 10 ml of a sterile specimen containing 1 mg/ml of the SE36 protein. This was stored as a stock solution for SE36 vaccine at 4° C. and supplied for subsequent assays. In SDS-polyacrylamide electrophoresis of the above specimen, several bands were visually detected in addition to a main band of 40 kd SE36 protein (FIG. 5). These bands all were confirmed to react with an anti-SE36 monoclonal antibody in the Western blotting analysis. Purity of the above specimen was estimated to be more than 99% (w/w).

In this connection, the protein concentration was calculated as 1 mg=0.491 ($OD_{278}$). This value was based on the fact that the SE36 molecule contains 1, 10 and 9 residues of Trp, Tyr and Phe, respectively, and the molecular extinction coefficient obtained from the sum of these residues was $\epsilon_{278}$=19160/mole.

Example 3

Determination of the Amino Acid Sequence

The N-terminal amino acid sequence of the SE36 protein prepared in Example 2 was determined by the Edman degradation using a protein sequencer Applied Biosystems 473A [PE Co., USA]. The results are shown in FIG. 2 and SEQ ID NO: 4 of Sequence Listing.

Example 4

Assays of Antigenicity and Immunogenicity

The antigenicity and immunogenicity of the SE36 protein in the vaccine stock solution prepared in Example 2 were assayed as shown in the following items (1) to (4).

(1) Preparation of Vaccine

The above vaccine stock solution was serially diluted 5 times with PBS to give solutions containing 200, 40, and 8 μg/0.05 ml of antigen. The solutions were mixed with an equal volume of Freund's complete adjuvant and Freund's incomplete adjuvant, respectively, to give emulsions. The former was used in the first immunization and the latter was used in the second and third immunization.

(2) Preparation of Mouse Immunized Sera

Using 20 female BALB/c mice [CLEA, Japan], the age of 7 weeks (5 mice/group, 4 groups in total), the above vaccine was inoculated subcutaneously in an amount of 0.1 ml/mouse 3 times, i.e., at first immunization, 7 days and 21 days after the first immunization. The 1st, 2nd and 3rd groups were inoculated subcutaneously with the vaccines containing 200 μg, 40 μg, and 8 μg of antigen, respectively. The 4th group was inoculated with 0.1 ml/mouse of a mixture of PBS and an adjuvant and used as a control group for comparison. 30 days after the 1st immunization, blood was collected from each mouse. The serum was individually inactivated by heating at 56° C. for 30 minutes, and stored at −20° C. The sera were used as murine anti-sera and a control murine serum for comparison in subsequent assays. All of the immunized mice of 1st to 3rd groups were healthy during breeding after inoculation with the vaccine as well as the 4th control group. No aberrant reduction of body weight, behavior, excreta, appearance, and fatal case were observed. Thus, the safety of the vaccine was confirmed.

(3) Blocking Test for Pf Growth

Honduras-1 strain of *Plasmodium falciparum* was used in this test, and cultured and maintained according to the method of Trager and Jensen (Science, 193, 673-675, 1976) and the method of Banyal and Inserberg (American Journal of Tropical and Medical Hygiene, 34, 1055-1064, 1985). When 80% of Pf-infented erythrocytes became trophozoite- and schizont-infected erythrocytes under culture, the maintenance medium was diluted with fresh erythrocytes to adjust the number of parasitic erythrocytes to 0.5% of the number of total blood cells. This was further diluted with the complete medium to adjust the erythrocyte concentration to 2% (v/v) to give a Pf-infected erythrocyte culture solution. This solution was dropwise added to a 96-well microplate at an amount of 100 μl/well, mixed with 1/20 volume (5 μl) of the murine anti-serum as described in the above item (2), and incubated at 37° C. for 72 hours. The above PBS-inoculated murine serum was used as a control for reference. After termination of the culture, this was applied on a slide and subjected to the Giemsa staining. On the slide, 5,000 erythrocytes were observed microscopically to count the number of Pf-infected erythrocytes. The blocking rate (%) for Pf growth was calculated from the following equation:

100×(1−the number of Pf-infected erythrocyte in murine antiserum/the number of Pf-infected erythrocyte in a control murine serum)

Using the above-counted Pf-infected erythrocyte number in the presence of the same dilution serum. As results, the above blocking rate by the respective murine antisera in the 1st and 2nd groups (5 mice/group) was 90%. The average value of 5 mice in the 3rd group was 70%. In this test, the murine antisera and the control murine serum were subjected to the following pretreatment prior to the above blocking test. To 0.5 ml each of the sera was added 2 ml of erythrocyte pack, and the mixture was kept at 37° C. for 2 hours, and then centrifuged (1500 rpm, 5 minutes) at room temperature to collect the supernatant. This was further mixed with 0.5 ml of fresh erythrocyte pack, and heated and centrifuged in the same manner as described above. The resulting supernatant was collected and used in the above blocking test.

(4) Antigen Analysis

ELISA and Western blotting analysis were conducted using a Vectastain ABC kit [Vector Laboratories, USA]. In ELISA, the SE36 protein was used as an antigen, and 2,2'-azino-bis-(3-ethylbenzothiaziline-6-sulfonic acid) was used as a substrate. The titer of ELISA was read at 505 nm with a microplate reader "Titertek Multiskan MCC/340 KM II" [Titerteck Scienfic, USA] and determined at an absorbance of 0.3. In Western blot analysis, diaminobenzidine tetrahydrochloride was used as a substrate.

The Pf-infected erythrocytes were obtained from a culture of the infected erythrocytes in which at least 80% of the parasite was mature trophozoite and schizont. The infected erythrocytes were dissolved in 0.075% (w/v) saponin solution under standing at 37° C. for 10 minutes, and then centrifuged (5000 g, 5 minutes) to give precipitate. The precipitate was suspended in PBS, and the suspension was mixed with a sample buffer solution for sodium dodecylsulfate-polyacrylamide electrophoresis (SDS-PAGE). This suspension was subjected to Western blot analysis as a malaria cell lysate.

In the above 1st to 3rd groups (5 mice/group), the average titer of ELISA was as follows: 1st group, 90000; 2nd group, 88,000; and 3rd group, 42000. In the 4th control group for reference, it was less than 100. The results of the Western blot analysis on the above malaria cell lysate indicated that a protein reacting with each murine antiserum of the 1st to 3rd groups was detected at 120 kd, and no protein reacting with each murine serum of the 4th group was detected at all. The above analysis was conducted by transferring the migrated band on SDS-PAGE using 12.5% (w/v) polyacrylamide to PVDF (polyvinylidene difluoride membrane filter), followed by reaction with the murine antiserum of the 1st to 3rd groups as well as the murine serum as a control for reference.

Example 5

Immune Test Using Chimpanzees

A test vaccine prepared by making the SE36 protein adsorb on aluminum hydroxide gel was inoculated to chimpanzees, and the blood collected at certain points in time was examined hematologically and hemato-biochemically. Their sera were also examined on immune response.

(1) Procedures

Using 3 chimpanzees, the trial vaccine was inoculated subcutaneously on their back at a dose of 450 μg (male, the age of 11 years), 50 μg (female, the age of 10 years), and 10 μg (female, the age of 6 years), respectively. As a test schedule, a booster inoculation was made 4 weeks after the 1st inoculation as 0 week. Collection of the blood was made prior to each inoculation and at the time of booster and with a lapse of time thereafter.

These tests were approved by an ethical committee at Sankyo Chemical Laboratories, Kumamoto Primate Park, and conducted at the institution attached to the laboratories.

(2) Results

Figure 6:
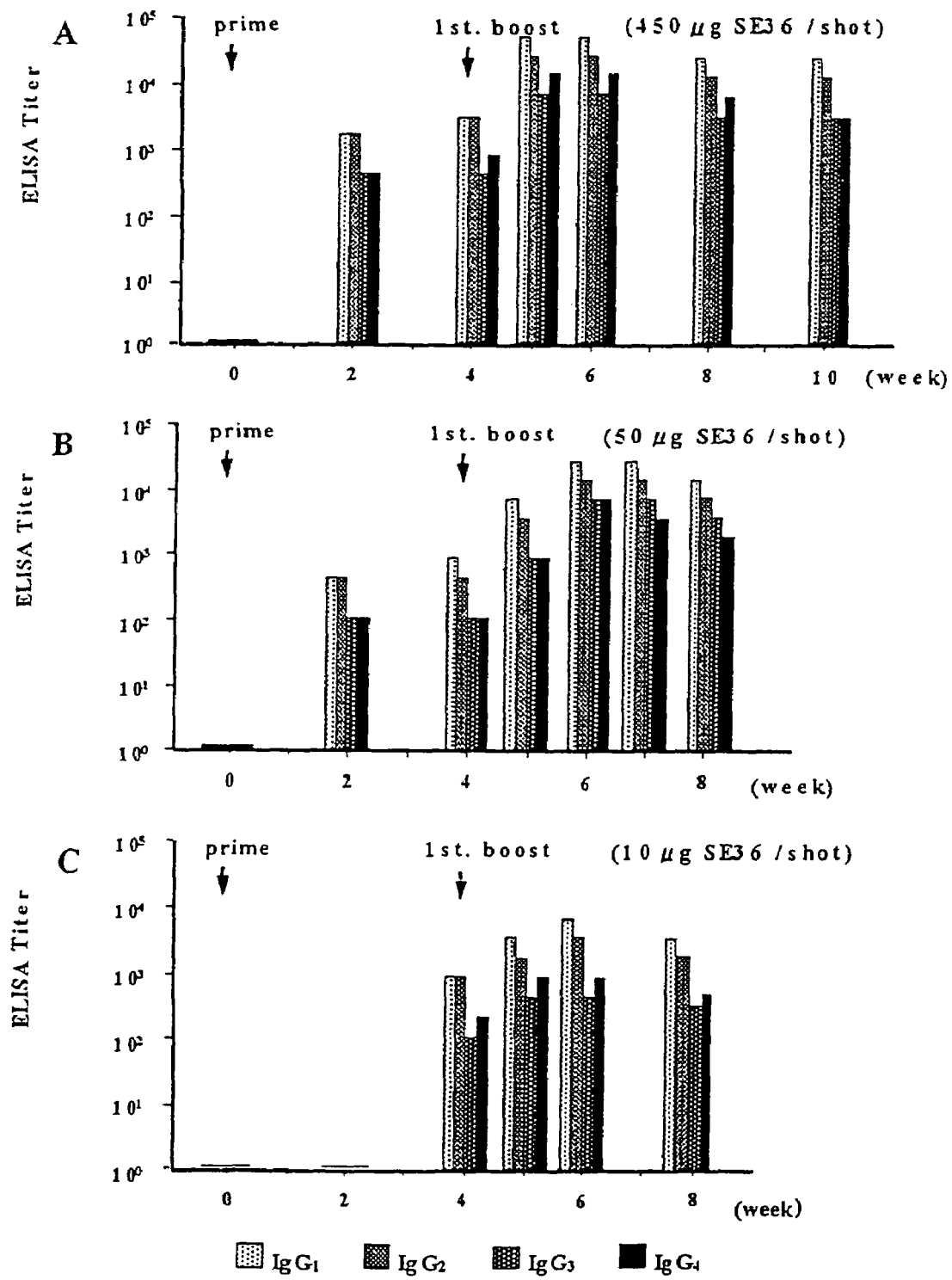
FIG. 6 is a graph showing each antibody titer of the IgG subclasses in chimpanzees immunized with an SE36 protein.

From the results of hematological and hemato-biochemical tests on the blood collected from the chimpanzees which were inoculated with the test vaccine, no trouble was confirmed even when the SE36 protein was inoculated at a dose as high as 450 μg/shot. From this result, it was confirmed that the vaccine that was prepared by malting the SE36 protein adsorb on aluminum hydroxide gel was safe. In addition, the specific antibody titer of the resulting sera for the SE36 protein was measured for the respective subclasses of IgG. As results, marked increase of the antibody titer was confirmed in all of the subclasses in the sera raised with 450 μg/shot. Particularly, the titer after 2nd inoculation reached approximately 10000-fold. This high antibody titer was maintained even after 10 weeks (FIG. 6A). Further, even in inoculation with 50 μg/shot, approximately the same immune response as that of 450 μg/shot was obtained (FIG. 6B). In inoculation with 10 μg/shot, the antibody titer was increased in all of the subclasses after 4 weeks and reached approximately 1,000-fold after 2nd inoculation, though somewhat long time was required for obtaining an immune response (FIG. 6C). From these results, it was confirmed that the vaccine of the invention permits induction of an immune response at a practical inoculation dose as a vaccine for human use.

In addition, an inhibitory test for growth of malaria parasite cells by IgG-dependent ADCI (Antibody-Dependent Cellular Inhibition of Parasite Growth) was conducted using an immune serum obtained by inoculation of 450 μg/shot. That is, an immune serum and monocytes ($2 \times 10^4$ cells/ml) were added to 100 μl of cultured solution of malaria parasite in erythrocites and incubated, and the number of the parasite cells after lapse of 48 hours was counted. In a test of immune sera of chimpanzees, the number of the parasite cells in a case of addition of 0.38 mg/ml of pre-immunized total IgG fraction was used as a control (100%) and the number of the parasite cells in the assay system was represented by the rate (%). In the assay system using a human serum acquiring immunity against malaria, the number of the parasite cells in a case of addition of 10 μg/ml of 3 fractions of non-specific IgG was used as a control (100%), and the number of the parasite cells was represented by the rate (%).

Figure 7:
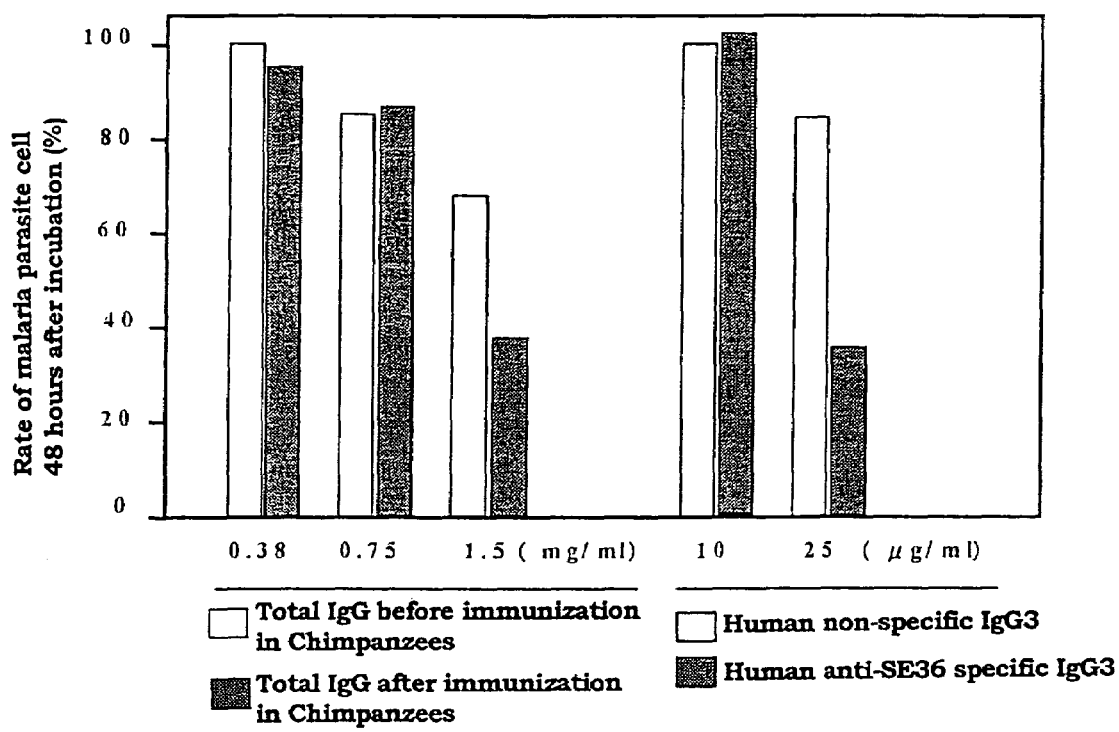
FIG. 7 is a graph showing the rate of inhibition against malaria protozoa in chimpanzees immunized with an SE36 protein and by human IgG acquiring malaria immunity.

The results are as shown in FIG. 7. When the total IgG collected before and after immunization in chimpanzees, 1.5 mg/ml each, was added, the growth was increased up to about 70% when the total IgG fraction before immunization was added, in comparison with a control. On the other hand, the growth was limited to about 40% when the total IgG fraction after immunization was added.

In the above test, the concentration of the added total IgG fraction of chimpanzees is about 1/10 of the IgG concentration in chimpanzee's sera. In comparison with the case of addition of the pre-immunized total IgG fraction, the addition of the post-immunized total IgG fraction produced better inhibition for the growth by about 30%. From these results, it is expected that in the in vivo blood almost perfect inhibitory effect could be obtained. If the use of IgG3 specific to the SE36 protein in measurement of human blood is taken into account, the inhibitory effect could be considered comparable to that of growth of the parasite in humans acquiring immunity against malaria. The above results confirmed the efficacy of the vaccine of the invention.

Reference Example 1

Epidemiological Examination I

Using the under 10 years old or less children's sera (average: 6 years old) in a highly malaria-infected area in Ugandam, the state of carrying a blood IgG3 antibody to the SE36 protein was examined by ELISA. As a result, it was found that out of 31 healthy children with no fever (body temperature: lower than 37.5° C.) 8 children were positive to IgG3 antibody, and on the other hand 9 patient children with fever (37.5° C. or higher) were negative to IgG3 antibody. These results indicated that the children producing or carrying an anti-SE36 IgG3 antibody had no fever at all, suggesting a correlation between the antibody and the inhibition of malaria occurrence.

Reference Example 2

Epidemiological Examination II

Using the blood collected from the under 15 years old or less children (86 cases) in the same area as above, a correlation between the number of blood parasites (Pf) and the antibody titer of an anti-SE36 IgG by ELISA was examined. The results suggested a correlation that as the antibody titer of the above IgG3 become higher, the blood Pf number was decreased.

Reference Example 3

Epidemiological Examination III

Using the sera of inhabitants in their respective age group (the age of 0 to 40 or higher) in a highly malaria-infected area, the state of carrying a blood antibody titer to the SE36 protein was examined by ELISA. As a result, it was found that the titer of anti-SE36 IgG3 antibody was always twice or higher than the flat or lower titer of other IgG1, IgG2 and IgG4 in the group of the age of 0 to 8. The titer further increased logarithmically with aging in the group over the age of 8.

Reference Example 4

Blocking Test for Growth of *falcipanum* Malaria Parasite

Figure 8:
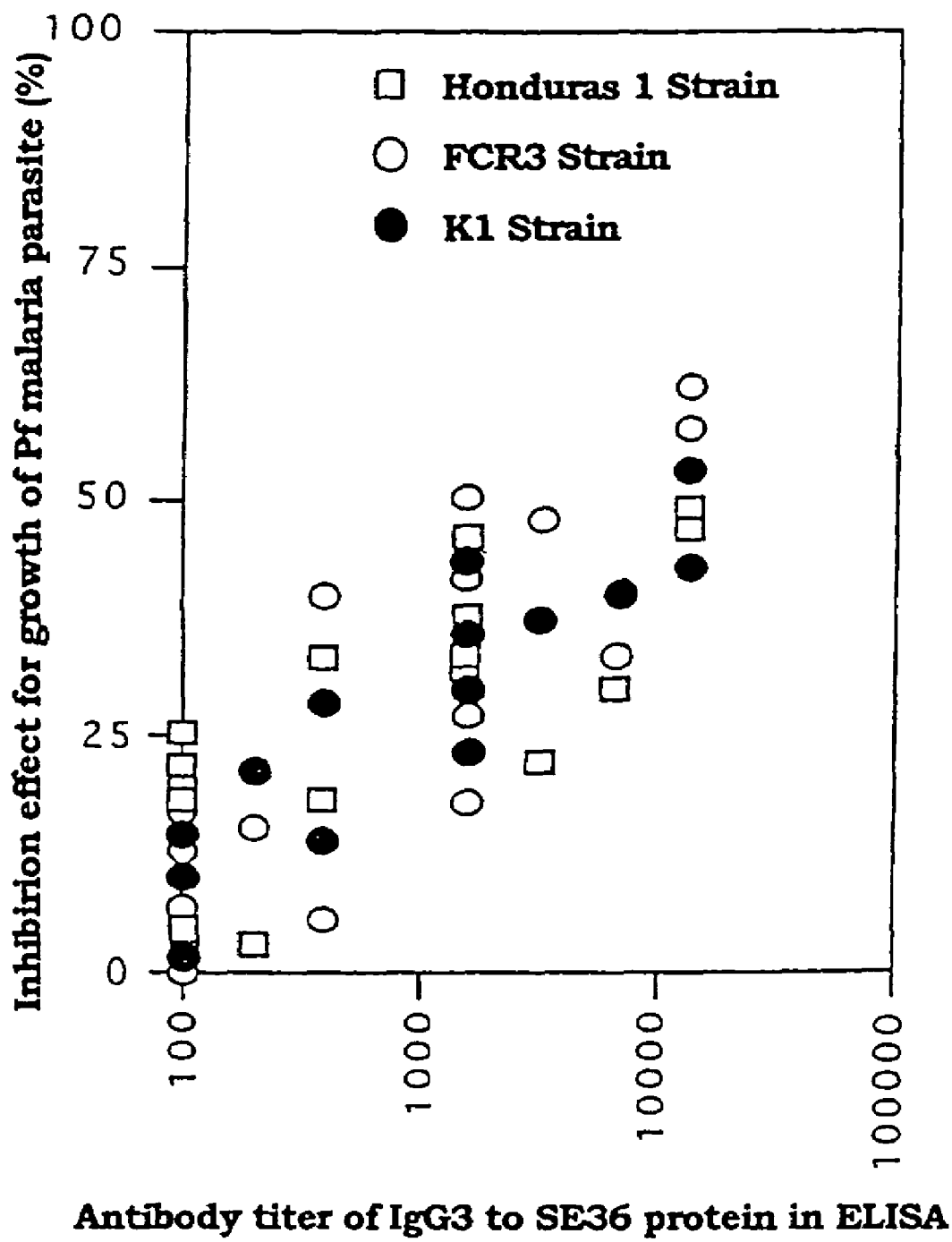
FIG. 8 shows that there is a positive correlation between the block of Pf protozoon's growth with the sera of inhabitants in a highly malaria-prevalent area and the antibody titer of an anti-SE36 IgG.

Using the sera of 25 inhabitants (adult) in a highly malaria-infected area, the state of carrying a blood antibody titer to the SE36 protein was examined by ELISA, and an in vitro blocking test for growth of *falciparum* malaria parasite was conducted using the same sera. Each serum in an amount corresponding to 5% of a culture medium was added to FCR3 strain, Honduras-1 strain, and K1 strain, respectively, and the blocking potency for growth of the parasite after 24 hours was examined using a serum of Japanese as a control that has no malaria immunity. As a result, it was found that all of the strains tested showed a positive correlation between the anti-SE36 IgG3 antibody and the blocking potency for growth, suggesting that the SE36 protein provided an epitope for a human antibody inhibiting growth of the parasite. Moreover, it was also suggested that genetic polymorphism of SERA had no effect on the vaccine activity (FIG. 8).

Reference Example 5

Neutralization Capacity of SE36

In the presence of the SE36 sterile specimen prepared in Example 2, prosperity and decline of the blocking potency for the Pf growth with a typical serum having a high anti-SE36 IgG3 antibody titer was examined with inhabitants in a highly malaria-infected area in the same manner as in the in vitro blocking test for growth of *falciparum* malaria parasite as described in Reference Example 4. As controls for comparison with SE36, the full length SERA protein having a natural steric structure produced by means of a Baculovirus vector and an SE50A protein (with no vaccine effect) derived from the central domain of the full length SERA protein (Vaccine, supra) were used, respectively.

Figure 9:
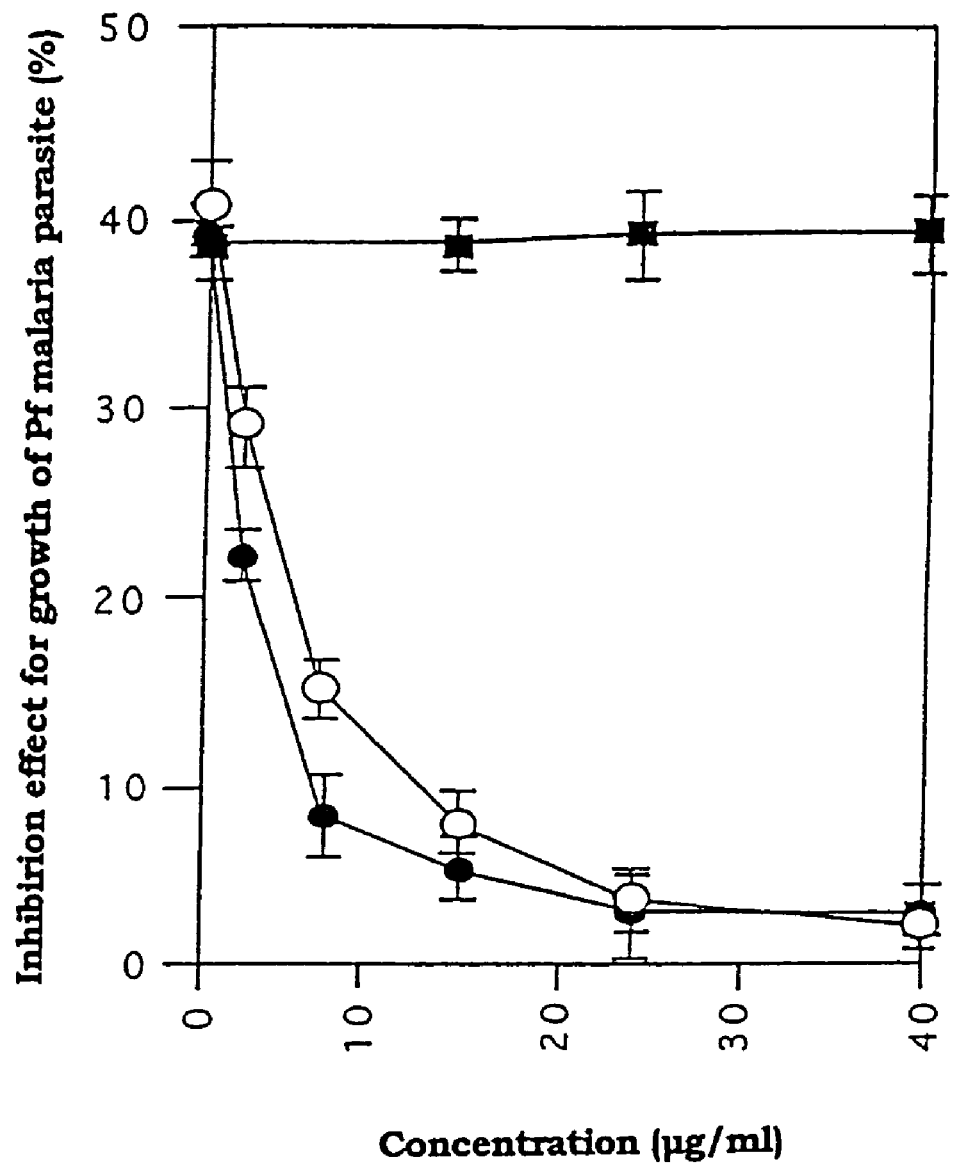
FIG. 9 shows that the block of Pf parasite growth with the sera of inhabitants in a highly malaria-prevalent area is markedly inhibited (neutralied) by the co-existence of an SE36 sterile specimen (vaccine stock solution) in comparison with a control.

As a result, it was found that the blocking potency to Pf growth in serum of the inhabitants in a highly malaria-infected area decreased (neutralized) greatly with increase of the co-existent SE36 concentration. On the other hand, no inhibition was observed with SE50A. The neutralization capacity of SE36 based on the degree of the above inhibition was superior to that of the full length SERA protein (FIG. 9).

INDUSTRIAL APPLICABILITY

The invention provides a highly preventive malaria vaccine which induces IgG3 antibodies inhibiting growth of malaria parasite (pf) in the red blood cells, said Pf growth being the basic cause of a malaria symptom with fever and cerebral malaria causing to death. Also, a diagnostic agent for malaria is provided. As a result, the cause of lethal cerebral malaria accompanied by the above Pf growth and fears of malaria can be dispelled. The invention, accordingly, contributes as a powerful means for controlling the world's most important multiple infectious diseases, malaria. Moreover, in these days when the expansion of malaria-occurring areas accompanied by global warming is feared, the invention will produce much desired effect and glad tidings on the health of humankind as well as assurance of global and healthy activities relative to tourism, economy, politics, etc.

The invention claimed is:

1. A synthetic polypeptide which consists of the amino acid sequence of SEQ ID NO: 4.

2. A synthetic polypeptide which consists of the amino acid sequence of SEQ ID NO: 4 with the following amino acid substitution: the 19th Glycine is substituted with a Valine.

* * * * *

SEQUENCE LISTING

<160> NUMBER OF SEQ ID NOS: 8

<210> SEQ ID NO 1
<211> LENGTH: 1146
<212> TYPE: DNA
<213> ORGANISM: Plasmodium falciparum
<220> FEATURE:
<221> NAME/KEY: CDS
<222> LOCATION: (1)..(1146)
<300> PUBLICATION INFORMATION:
<301> AUTHORS: Li, W. B. et al.
<302> TITLE: Structure and expression of Plasmodium falciparum SERA gene
<303> JOURNAL: Mol. Biochem. Parasitol.
<304> VOLUME: 33
<305> ISSUE: 1
<306> PAGES: 13-25
<307> DATE: Winter-1989
<308> DATABASE ACCESSION NUMBER: GenBank/J04000
<309> DATABASE ENTRY DATE: 1994-03-15

<400> SEQUENCE: 1

```
atg aag tca tat att tcc ttg ttt ttc ata ttg tgt gtt ata ttt aac        48
Met Lys Ser Tyr Ile Ser Leu Phe Phe Ile Leu Cys Val Ile Phe Asn
 1               5                  10                  15 aaa aat gtt ata aaa tgt aca gga gaa agt caa aca ggt aat aca gga        96
Lys Asn Val Ile Lys Cys Thr Gly Glu Ser Gln Thr Gly Asn Thr Gly
             20                  25                  30 gga ggt caa gca ggt aat aca gta gga gat caa gca ggt agt aca gga       144
Gly Gly Gln Ala Gly Asn Thr Val Gly Asp Gln Ala Gly Ser Thr Gly
         35                  40                  45 gga agt cca caa ggt agt acg gga gca agt caa ccc gga agt tcc gaa       192
Gly Ser Pro Gln Gly Ser Thr Gly Ala Ser Gln Pro Gly Ser Ser Glu
     50                  55                  60 cca agc aat cct gta agt tcc gga cat tct gta agt act gta tca gta       240
Pro Ser Asn Pro Val Ser Ser Gly His Ser Val Ser Thr Val Ser Val
 65                  70                  75                  80 tca caa act tca act tct tca gaa aaa cag gat aca att caa gta aaa       288
Ser Gln Thr Ser Thr Ser Ser Glu Lys Gln Asp Thr Ile Gln Val Lys
                 85                  90                  95 tca gct tta tta aaa gat tat atg ggt tta aaa gtt act ggt cca tgt       336
Ser Ala Leu Leu Lys Asp Tyr Met Gly Leu Lys Val Thr Gly Pro Cys
            100                 105                 110 aac gaa aat ttc ata atg ttc tta gtt cct cat ata tat att gat gtt       384
Asn Glu Asn Phe Ile Met Phe Leu Val Pro His Ile Tyr Ile Asp Val
        115                 120                 125 gat aca gaa gat act aat atc gaa tta aga aca aca ttg aaa gaa aca       432
Asp Thr Glu Asp Thr Asn Ile Glu Leu Arg Thr Thr Leu Lys Glu Thr
    130                 135                 140 aat aat gca ata tca ttt gaa tca aac agt ggt tca tta gaa aaa aaa       480
Asn Asn Ala Ile Ser Phe Glu Ser Asn Ser Gly Ser Leu Glu Lys Lys
145                 150                 155                 160 aaa tat gta aaa cta cca tca aat ggt aca act ggt gaa caa ggt tca       528
Lys Tyr Val Lys Leu Pro Ser Asn Gly Thr Thr Gly Glu Gln Gly Ser
                165                 170                 175 agt acg gga aca gtt aga gga gat aca gaa cca att tca gat tca agc       576
Ser Thr Gly Thr Val Arg Gly Asp Thr Glu Pro Ile Ser Asp Ser Ser
            180                 185                 190 tca agt tca agt tca agt tct agt tca agt tca agt tca agt tct agt       624
Ser Ser Ser Ser Ser Ser Ser Ser Ser Ser Ser Ser Ser Ser Ser Ser
        195                 200                 205 tca agt tca agt tca agt tca agt tct agt tca agt tct agt tca agt       672
Ser Ser Ser Ser Ser Ser Ser Ser Ser Ser Ser Ser Ser Ser Ser Ser
```

```
            210                 215                 220
tca gaa agt ctt cct gct aat gga cct gat tcc cct act gtt aaa ccg    720
Ser Glu Ser Leu Pro Ala Asn Gly Pro Asp Ser Pro Thr Val Lys Pro
225                 230                 235                 240 cca aga aat tta caa aat ata tgt gaa act gga aaa aac ttc aag ttg    768
Pro Arg Asn Leu Gln Asn Ile Cys Glu Thr Gly Lys Asn Phe Lys Leu
                245                 250                 255 gta gta tat att aag gag aat aca tta ata att aaa tgg aaa gta tac    816
Val Val Tyr Ile Lys Glu Asn Thr Leu Ile Ile Lys Trp Lys Val Tyr
            260                 265                 270 gga gaa aca aaa gat act act gaa aat aac aaa gtt gat gta aga aag    864
Gly Glu Thr Lys Asp Thr Thr Glu Asn Asn Lys Val Asp Val Arg Lys
        275                 280                 285 tat ttg ata aat gaa aag gaa acc cca ttt act agt ata cta ata cat    912
Tyr Leu Ile Asn Glu Lys Glu Thr Pro Phe Thr Ser Ile Leu Ile His
    290                 295                 300 gcg tat aaa gaa cat aat gga aca aac tta ata gaa agt aaa aac tac    960
Ala Tyr Lys Glu His Asn Gly Thr Asn Leu Ile Glu Ser Lys Asn Tyr
305                 310                 315                 320 gca tta gga tca gac att cca gaa aaa tgt gat acc tta gct tcc aat   1008
Ala Leu Gly Ser Asp Ile Pro Glu Lys Cys Asp Thr Leu Ala Ser Asn
                325                 330                 335 tgc ttt tta agt ggt aat ttt aac att gaa aaa tgc ttt caa tgt gct   1056
Cys Phe Leu Ser Gly Asn Phe Asn Ile Glu Lys Cys Phe Gln Cys Ala
            340                 345                 350 ctt tta gta gaa aaa gaa aat aaa aat gac gta tgt tac aaa tac cta   1104
Leu Leu Val Glu Lys Glu Asn Lys Asn Asp Val Cys Tyr Lys Tyr Leu
        355                 360                 365 tct gaa gat att gta agt aac ttc aaa gaa ata aaa gct gag           1146
Ser Glu Asp Ile Val Ser Asn Phe Lys Glu Ile Lys Ala Glu
    370                 375                 380

<210> SEQ ID NO 2
<211> LENGTH: 382
<212> TYPE: PRT
<213> ORGANISM: Plasmodium falciparum

<400> SEQUENCE: 2

Met Lys Ser Tyr Ile Ser Leu Phe Phe Ile Leu Cys Val Ile Phe Asn
1               5                   10                  15

Lys Asn Val Ile Lys Cys Thr Gly Glu Ser Gln Thr Gly Asn Thr Gly
            20                  25                  30

Gly Gly Gln Ala Gly Asn Thr Val Gly Asp Gln Ala Gly Ser Thr Gly
        35                  40                  45

Gly Ser Pro Gln Gly Ser Thr Gly Ala Ser Gln Pro Gly Ser Ser Glu
    50                  55                  60

Pro Ser Asn Pro Val Ser Ser Gly His Ser Val Ser Thr Val Ser Val
65                  70                  75                  80

Ser Gln Thr Ser Thr Ser Ser Glu Lys Gln Asp Thr Ile Gln Val Lys
                85                  90                  95

Ser Ala Leu Leu Lys Asp Tyr Met Gly Leu Lys Val Thr Gly Pro Cys
            100                 105                 110

Asn Glu Asn Phe Ile Met Phe Leu Val Pro His Ile Tyr Ile Asp Val
        115                 120                 125

Asp Thr Glu Asp Thr Asn Ile Glu Leu Arg Thr Thr Leu Lys Glu Thr
    130                 135                 140

Asn Asn Ala Ile Ser Phe Glu Ser Asn Ser Gly Ser Leu Glu Lys Lys
145                 150                 155                 160
```

```
Lys Tyr Val Lys Leu Pro Ser Asn Gly Thr Thr Gly Glu Gln Gly Ser
            165                 170                 175

Ser Thr Gly Thr Val Arg Gly Asp Thr Glu Pro Ile Ser Asp Ser Ser
        180                 185                 190

Ser Ser Ser Ser Ser Ser Ser Ser Ser Ser Ser Ser Ser Ser Ser Ser
    195                 200                 205

Ser Ser Ser Ser Ser Ser Ser Ser Ser Ser Ser Ser Ser Ser Ser Ser
    210                 215                 220

Ser Glu Ser Leu Pro Ala Asn Gly Pro Asp Ser Pro Thr Val Lys Pro
225                 230                 235                 240

Pro Arg Asn Leu Gln Asn Ile Cys Glu Thr Gly Lys Asn Phe Lys Leu
                245                 250                 255

Val Val Tyr Ile Lys Glu Asn Thr Leu Ile Ile Lys Trp Lys Val Tyr
            260                 265                 270

Gly Glu Thr Lys Asp Thr Thr Glu Asn Asn Lys Val Asp Val Arg Lys
        275                 280                 285

Tyr Leu Ile Asn Glu Lys Glu Thr Pro Phe Thr Ser Ile Leu Ile His
    290                 295                 300

Ala Tyr Lys Glu His Asn Gly Thr Asn Leu Ile Glu Ser Lys Asn Tyr
305                 310                 315                 320

Ala Leu Gly Ser Asp Ile Pro Glu Lys Cys Asp Thr Leu Ala Ser Asn
                325                 330                 335

Cys Phe Leu Ser Gly Asn Phe Asn Ile Glu Lys Cys Phe Gln Cys Ala
            340                 345                 350

Leu Leu Val Glu Lys Glu Asn Lys Asn Asp Val Cys Tyr Lys Tyr Leu
        355                 360                 365

Ser Glu Asp Ile Val Ser Asn Phe Lys Glu Ile Lys Ala Glu
    370                 375                 380

<210> SEQ ID NO 3
<211> LENGTH: 1005
<212> TYPE: DNA
<213> ORGANISM: Artificial Sequence
<220> FEATURE:
<221> NAME/KEY: CDS
<222> LOCATION: (1)..(1002)
<220> FEATURE:
<223> OTHER INFORMATION: Description of Artificial Sequence: SE36
      Genetic DNA

<400> SEQUENCE: 3 atg aaa aac gtg atc aaa tgt acc ggt gaa agc cag acc ggt aat acc      48
Met Lys Asn Val Ile Lys Cys Thr Gly Glu Ser Gln Thr Gly Asn Thr
 1               5                  10                  15 ggc ggt ggt cag gca ggc aac acg gtt ggc gac cag gcg ggc tct acc      96
Gly Gly Gly Gln Ala Gly Asn Thr Val Gly Asp Gln Ala Gly Ser Thr
            20                  25                  30 ggc ggc tct ccg cag ggt agc aca ggc gcc agt caa ccc ggc tct agc     144
Gly Gly Ser Pro Gln Gly Ser Thr Gly Ala Ser Gln Pro Gly Ser Ser
        35                  40                  45 gaa ccg tct aac cca gtg tct tct ggc cat tct gtt agt acc gtt agc     192
Glu Pro Ser Asn Pro Val Ser Ser Gly His Ser Val Ser Thr Val Ser
    50                  55                  60 gtt agc cag acc agc acc tct tct gaa aaa caa gat acc att cag gtg     240
Val Ser Gln Thr Ser Thr Ser Ser Glu Lys Gln Asp Thr Ile Gln Val
65                  70                  75                  80 aaa tct gcg ctg ctg aaa gat tat atg ggt tta aaa gtt acg ggc ccg     288
Lys Ser Ala Leu Leu Lys Asp Tyr Met Gly Leu Lys Val Thr Gly Pro
```

```
                       85                  90                  95
tgt aac gaa aat ttc atc atg ttc ctg gtt ccg cat att tat att gat    336
Cys Asn Glu Asn Phe Ile Met Phe Leu Val Pro His Ile Tyr Ile Asp
            100                 105                 110 gtg gat acc gaa gat acc aat ata gag ctc cgt acc acc ctg aaa gaa    384
Val Asp Thr Glu Asp Thr Asn Ile Glu Leu Arg Thr Thr Leu Lys Glu
                115                 120                 125 acc aac aac gcg atc tca ttt gaa tca aac agt ggt tca ctg gaa aaa    432
Thr Asn Asn Ala Ile Ser Phe Glu Ser Asn Ser Gly Ser Leu Glu Lys
        130                 135                 140 aaa aaa tat gtg aag ctt ccg tca aac ggc acc acc ggt gaa cag ggt    480
Lys Lys Tyr Val Lys Leu Pro Ser Asn Gly Thr Thr Gly Glu Gln Gly
145                 150                 155                 160 tca agt aca ggc acc gtt cgc ggc gat acc gaa ccg att tca gac tcg    528
Ser Ser Thr Gly Thr Val Arg Gly Asp Thr Glu Pro Ile Ser Asp Ser
                165                 170                 175 agt gaa agt ctt ccg gcg aat ggc ccg gat tcc ccg acc gtt aaa ccc    576
Ser Glu Ser Leu Pro Ala Asn Gly Pro Asp Ser Pro Thr Val Lys Pro
            180                 185                 190 ccg cgt aac ctg cag aac atc tgt gaa acc ggc aaa aac ttc aaa ctg    624
Pro Arg Asn Leu Gln Asn Ile Cys Glu Thr Gly Lys Asn Phe Lys Leu
        195                 200                 205 gtg gtg tat att aag gag aat aca tta atc att aaa tgg aaa gtg tac    672
Val Val Tyr Ile Lys Glu Asn Thr Leu Ile Ile Lys Trp Lys Val Tyr
210                 215                 220 ggc gaa acc aaa gat acc acc gaa aat aac aaa gtg gac gta cgc aag    720
Gly Glu Thr Lys Asp Thr Thr Glu Asn Asn Lys Val Asp Val Arg Lys
                225                 230                 235                 240 tat ctg att aac gaa aag gaa acc ccg ttt act agt att cta atc cat    768
Tyr Leu Ile Asn Glu Lys Glu Thr Pro Phe Thr Ser Ile Leu Ile His
            245                 250                 255 gca tat aaa gaa cat aat ggc acc aac ctg atc gaa agt aaa aac tac    816
Ala Tyr Lys Glu His Asn Gly Thr Asn Leu Ile Glu Ser Lys Asn Tyr
        260                 265                 270 gcg ctg ggc tca gac att ccg gaa aaa tgt gat acc ctg gcg tcc aat    864
Ala Leu Gly Ser Asp Ile Pro Glu Lys Cys Asp Thr Leu Ala Ser Asn
    275                 280                 285 tgc ttt ctg agt ggt aac ttt aac att gaa aaa tgc ttt cag tgc gcg    912
Cys Phe Leu Ser Gly Asn Phe Asn Ile Glu Lys Cys Phe Gln Cys Ala
290                 295                 300 ctg ctg gtg gaa aaa gaa aat aaa aac gac gtg tgt tac aaa tac cta    960
Leu Leu Val Glu Lys Glu Asn Lys Asn Asp Val Cys Tyr Lys Tyr Leu
305                 310                 315                 320 agc gaa gat att gtg tct aat ttc aag gag atc aaa gcg gag taa        1005
Ser Glu Asp Ile Val Ser Asn Phe Lys Glu Ile Lys Ala Glu
                325                 330

<210> SEQ ID NO 4
<211> LENGTH: 334
<212> TYPE: PRT
<213> ORGANISM: Artificial Sequence
<220> FEATURE:
<223> OTHER INFORMATION: Description of Artificial Sequence: SE36
      Genetic DNA

<400> SEQUENCE: 4

Met Lys Asn Val Ile Lys Cys Thr Gly Glu Ser Gln Thr Gly Asn Thr
 1               5                  10                  15

Gly Gly Gly Gln Ala Gly Asn Thr Val Gly Asp Gln Ala Gly Ser Thr
            20                  25                  30
```

-continued

Gly Gly Ser Pro Gln Gly Ser Thr Gly Ala Ser Gln Pro Gly Ser Ser
          35                  40                  45

Glu Pro Ser Asn Pro Val Ser Ser Gly His Ser Val Ser Thr Val Ser
 50                  55                  60

Val Ser Gln Thr Ser Thr Ser Ser Glu Lys Gln Asp Thr Ile Gln Val
 65                  70                  75                  80

Lys Ser Ala Leu Leu Lys Asp Tyr Met Gly Leu Lys Val Thr Gly Pro
                 85                  90                  95

Cys Asn Glu Asn Phe Ile Met Phe Leu Val Pro His Ile Tyr Ile Asp
                100                 105                 110

Val Asp Thr Glu Asp Thr Asn Ile Glu Leu Arg Thr Thr Leu Lys Glu
            115                 120                 125

Thr Asn Asn Ala Ile Ser Phe Glu Ser Asn Ser Gly Ser Leu Glu Lys
        130                 135                 140

Lys Lys Tyr Val Lys Leu Pro Ser Asn Gly Thr Thr Gly Gln Gly
145                 150                 155                 160

Ser Ser Thr Gly Thr Val Arg Gly Asp Thr Glu Pro Ile Ser Asp Ser
                165                 170                 175

Ser Glu Ser Leu Pro Ala Asn Gly Pro Asp Ser Pro Thr Val Lys Pro
            180                 185                 190

Pro Arg Asn Leu Gln Asn Ile Cys Glu Thr Gly Lys Asn Phe Lys Leu
        195                 200                 205

Val Val Tyr Ile Lys Glu Asn Thr Leu Ile Ile Lys Trp Lys Val Tyr
    210                 215                 220

Gly Glu Thr Lys Asp Thr Thr Glu Asn Asn Lys Val Asp Val Arg Lys
225                 230                 235                 240

Tyr Leu Ile Asn Glu Lys Glu Thr Pro Phe Thr Ser Ile Leu Ile His
                245                 250                 255

Ala Tyr Lys Glu His Asn Gly Thr Asn Leu Ile Glu Ser Lys Asn Tyr
            260                 265                 270

Ala Leu Gly Ser Asp Ile Pro Glu Lys Cys Asp Thr Leu Ala Ser Asn
        275                 280                 285

Cys Phe Leu Ser Gly Asn Phe Asn Ile Glu Lys Cys Phe Gln Cys Ala
    290                 295                 300

Leu Leu Val Glu Lys Glu Asn Lys Asn Asp Val Cys Tyr Lys Tyr Leu
305                 310                 315                 320

Ser Glu Asp Ile Val Ser Asn Phe Lys Glu Ile Lys Ala Glu
                325                 330

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: SE36
      Genetic DNA

<400> SEQUENCE: 5

Gly Gln Ala Gly Asn Thr Gly Gly
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: SE36
      Genetic DNA

```
<400> SEQUENCE: 6

Gly Gln Ala Gly Asn Thr Val Gly
  1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: SE36
      Genetic DNA

<400> SEQUENCE: 7

Ser Pro Gln Gly Ser Thr Gly Ala
  1               5

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: SE36
      Genetic DNA

<400> SEQUENCE: 8

Ser Pro Gln Gly Ser Thr Gly Ala Ser Pro Gln Gly Ser Thr Gly Ala
  1               5                  10                  15
```